US 8,921,099 B2

(12) United States Patent
Ootani et al.

(10) Patent No.: US 8,921,099 B2
(45) Date of Patent: Dec. 30, 2014

(54) CELL ANALYZER, CELL PROCESSING APPARATUS, SPECIMEN PREPARING APPARATUS

(71) Applicant: Sysmex Corporation, Kobe (JP)

(72) Inventors: Toshihiro Ootani, Kobe (JP); Ryuichiro Ebi, Kobe (JP); Koki Tajima, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 13/845,806

(22) Filed: Mar. 18, 2013

(65) Prior Publication Data

US 2013/0217110 A1    Aug. 22, 2013

Related U.S. Application Data

(63) Continuation of application No. PCT/JP2011/004868, filed on Aug. 31, 2011.

(30) Foreign Application Priority Data

Sep. 22, 2010  (JP) ................... 2010-212613

(51) Int. Cl.
| | | |
|---|---|---|
| G01N 21/47 | (2006.01) | |
| G01N 15/14 | (2006.01) | |
| G01N 35/02 | (2006.01) | |
| G01N 21/64 | (2006.01) | |
| G01N 35/00 | (2006.01) | |

(52) U.S. Cl.
CPC .......... G01N 21/4738 (2013.01); *G01N 35/025* (2013.01); *G01N 2021/6439* (2013.01); *G01N 2021/4707* (2013.01); *G01N 2035/00356* (2013.01); G01N 21/47 (2013.01); G01N 15/14 (2013.01); *G01N 2021/4726* (2013.01); *G01N 21/6428* (2013.01); *G01N 2035/00554* (2013.01)

USPC ..................................... 435/288.7; 435/283.1

(58) Field of Classification Search
CPC .... G01N 21/4738; G01N 15/14; G01N 21/47
See application file for complete search history.

(56) References Cited

U.S. PATENT DOCUMENTS 5,139,031 A * 8/1992 Guirguis ....................... 600/584
5,328,826 A    7/1994 Nozawa et al.
(Continued)

FOREIGN PATENT DOCUMENTS

| CN | 1425061 A | 6/2003 |
|---|---|---|
| CN | 1677109 A | 10/2005 |

(Continued)

OTHER PUBLICATIONS

International Search Report for International Application No. PCT/JP2011/004868, dated Oct. 4, 2011, 4 pages.

(Continued)

*Primary Examiner* — Nathan Bowers
*Assistant Examiner* — Gautam Prakash
(74) *Attorney, Agent, or Firm* — Brinks Gilson & Lione

(57) ABSTRACT

The present invention provides a cell analyzer which comprises: a cell dispersion unit which causes aggregated cells in a biological specimen to be dispersed, through a shearing force applying process of applying a shearing force to the aggregated cells and an ultrasonic dispersion process of dispersing the aggregated cells, by using ultrasonic waves; a detection unit which detects characteristics information reflecting properties of the cells in the biological specimen on which the shearing force applying process and the ultrasonic dispersion process have been performed; and an analysis unit which analyzes the cells in the biological specimen, based on a detection result from the detection unit.

10 Claims, 17 Drawing Sheets

(56) References Cited

U.S. PATENT DOCUMENTS

| | | | |
|---|---|---|---|
| 6,255,614 B1 * | 7/2001 | Yamakawa et al. | 209/587 |
| 6,436,704 B1 | 8/2002 | Roberts et al. | |
| 6,872,565 B2 * | 3/2005 | Mollstam et al. | 435/252.9 |
| 2005/0221399 A1 | 10/2005 | Nakano et al. | |
| 2009/0215053 A1 | 8/2009 | Galon et al. | |
| 2011/0014685 A1 | 1/2011 | Fukuda et al. | |
| 2011/0033428 A1 | 2/2011 | Maruyama et al. | |

FOREIGN PATENT DOCUMENTS

| | | |
|---|---|---|
| EP | 1905824 A1 | 4/2008 |
| EP | 2261632 A1 | 12/2010 |
| EP | 2306188 A1 | 4/2011 |
| JP | 63-168563 A | 7/1988 |
| JP | 04-076458 A | 3/1992 |
| JP | 05-080053 A | 3/1993 |
| JP | 2005-315862 A | 11/2005 |
| JP | 2008-249543 A | 10/2008 |
| JP | 2009-515148 A | 4/2009 |
| JP | 2009-192450 A | 8/2009 |
| WO | WO 2006/129735 A1 | 12/2006 |
| WO | WO 2007/045996 A1 | 4/2007 |
| WO | WO 2009/123000 A1 | 10/2009 |
| WO | WO 2009/125877 A1 | 10/2009 |
| WO | WO 2010/005078 A1 | 1/2010 |

OTHER PUBLICATIONS

International Preliminary Report on Patentability for International Application No. PCT/JP2011/004868, dated Apr. 16, 2013, 9 pages.

* cited by examiner

CELL ANALYZER, CELL PROCESSING APPARATUS, SPECIMEN PREPARING APPARATUS

RELATED APPLICATIONS

This application is a continuation of PCT/JP2011/004868 filed on Aug. 31, 2011, which claims priority to Japanese Application No. 2010-212623 filed on Sep. 22, 2010. The entire contents of these applications are incorporated herein by reference.

FIELD OF THE INVENTION

The present invention relates to cell analyzers, and in particular, to cell analyzers that analyze cells contained in a biological specimen collected from an organism.

BACKGROUND OF THE INVENTION

As a cell analyzer that analyzes cells contained in a biological specimen collected from an organism, there has been conventionally known a cell analyzer that screens cancer cells or atypical cells by measuring, with a flow cytometer, epithelial cells of the uterine cervix contained in a specimen collected from the uterine cervix of a subject (see Patent Literature 1, for example).

The cell analyzer described in Patent Literature 1 (US Patent Application Publication No. 2011/0014685) above includes: a cell dispersion unit which actively causes aggregated cells of a biological specimen to be dispersed in a biological specimen container; a flow cytometer which perform measurement of cells dispersed in a measurement specimen, which have been subjected to the dispersion process through the cell dispersion unit; and a data processing apparatus which analyzes measured data from the flow cytometer to determine whether or not cells in the specimen are cancerous.

The cell analyzer described in Patent Literature 1 allows for a determination of whether or not cells in the measurement specimen are cancerous. However, cells highly aggregated in a biological specimen are not to be dispersed in an appropriate manner. This results in impaired degree of accuracy in the analysis. Therefore, it is desired that highly accurate cell analysis can be performed even when cells in a biological specimen are aggregated at a high level.

SUMMARY OF THE INVENTION

The scope of the present invention is defined solely by the appended claims, and is not affected to any degree by the statements within this summary.

A first aspect of the present invention is a cell analyzer comprising: a cell dispersion unit which causes aggregated cells in a biological specimen to be dispersed, through a shearing force applying process of applying a shearing force to the aggregated cells and an ultrasonic dispersion process of dispersing the aggregated cells, by using ultrasonic waves; a detection unit which detects characteristics information reflecting properties of the cells in the biological specimen on which the shearing force applying process and the ultrasonic dispersion process have been performed; and an analysis unit which analyzes the cells in the biological specimen, based on a detection result from the detection unit.

A second aspect of the present invention is a cell processing apparatus, comprising: a first dispersion unit which applies a shearing force to aggregated cells in a biological specimen; and a second dispersion unit which disperses the aggregated cells by using ultrasonic waves.

A third aspect of the present invention is a specimen preparing apparatus, comprising: a first dispersion unit which applies a shearing force to aggregated cells in a biological specimen; a second dispersion unit which disperses the aggregated cells by using ultrasonic waves; and a specimen preparation unit which prepares a measurement specimen from the biological specimen after the aggregated cells in the biological specimen have been dispersed by the first dispersion unit and the second dispersion unit.

DETAILED DESCRIPTION OF THE PREFERRED EMBODIMENT

Hereinafter, specific embodiments of the present invention will be described with reference to the drawings.

First Embodiment

First, with reference to FIGS. 1 to 15, a configuration of a cell analyzer 1 according to a first embodiment of the present invention will be described.

The cell analyzer 1 causes a measurement specimen containing cells collected from a patient, to flow through a flow cell; and the analyzer emits a beam of laser right onto the measurement specimen streaming through the flow cell. Then, the analyzer detects lights (forward scattered light, side fluorescence, etc.) from the measurement specimen, analyzes the light signals and determines whether or not cancer cells are included in the cells. More specifically, the cell analyzer 1 according to the first embodiment targets epithelial cells of the uterine cervix as its analyte, and is used for screening cervical cancer.

Figure 1:
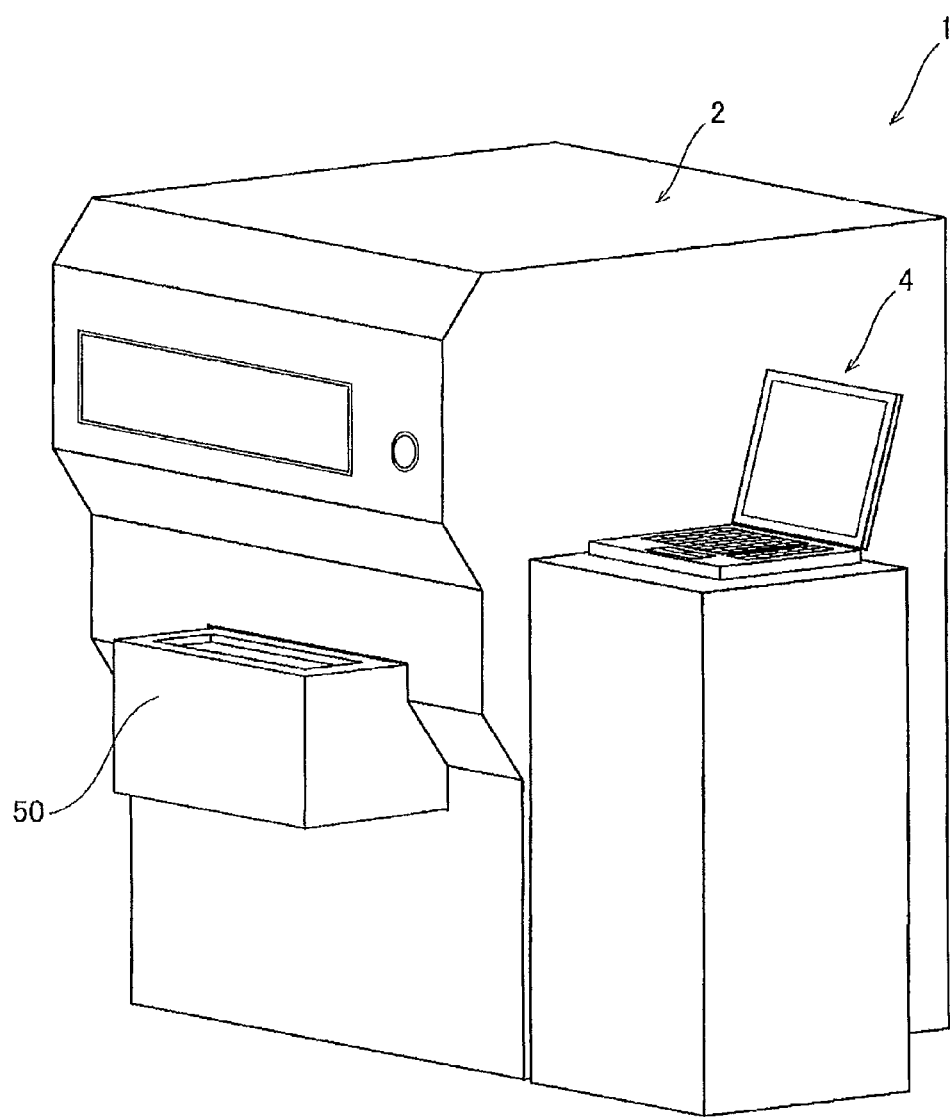
FIG. 1 is a perspective view showing an overall structure of a cell analyzer according to a first embodiment of the present invention.

As shown in FIG. 1, the cell analyzer 1 includes: a measuring apparatus 2 which applies a cell dispersion process, a staining process, etc. to a biological specimen collected from the uterine cervix of a subject to prepare a measurement specimen, and which also performs optical measurement on the measurement specimen using a laser beam; and a data processing apparatus 4 which analyzes measurement results obtained through the measuring apparatus 2.

Figure 2:
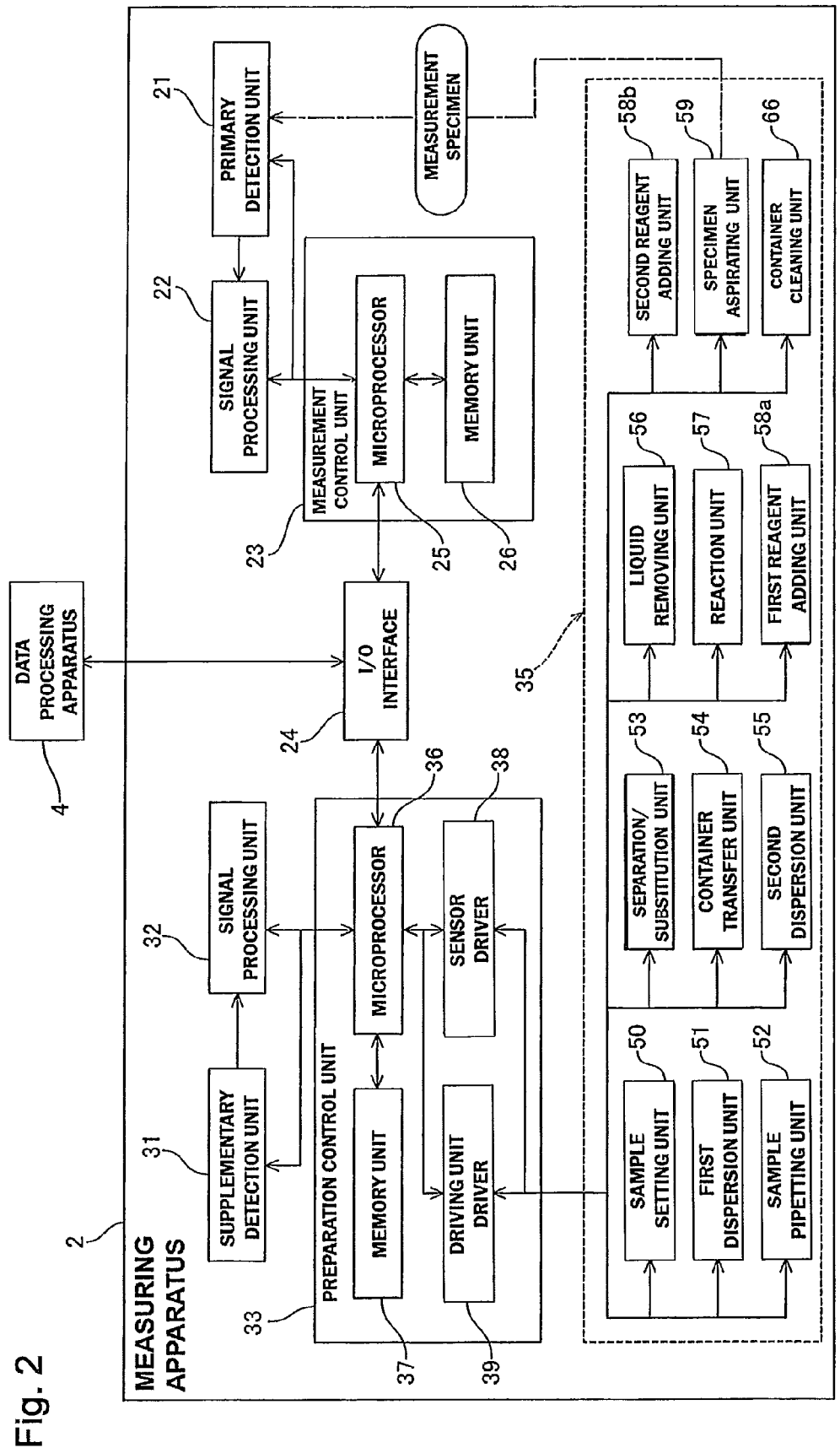
FIG. 2 is a block diagram showing a configuration of a measuring apparatus of the cell analyzer shown in FIG. 1.

As shown in FIG. 2, the measuring apparatus 2 includes a primary detection unit 21, a signal processing unit 22, a measurement control unit 23, and an I/O interface 24. Further, the measuring apparatus 2 includes a supplementary detection unit 31, a signal processing unit 32, a preparation control unit 33, and a preparation device unit 35 for automatically adjusting components for a biological specimen.

Figure 5:
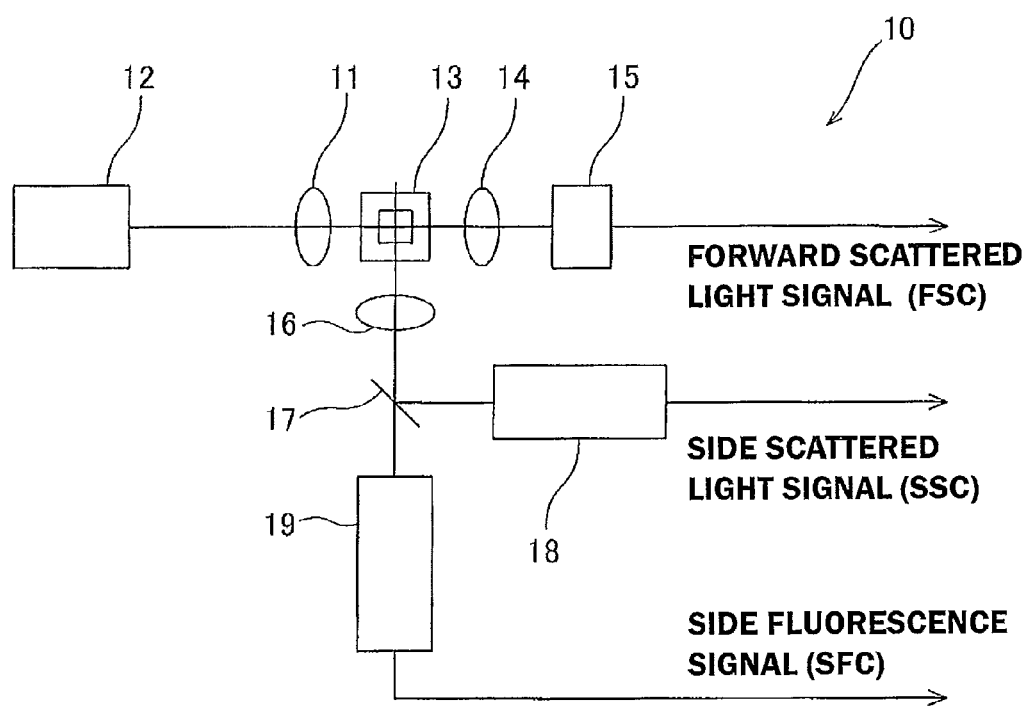
FIG. 5 is a schematic diagram showing a flow cytometer forming a primary detection unit of the measuring apparatus shown in FIG. 2.
Figure 6:
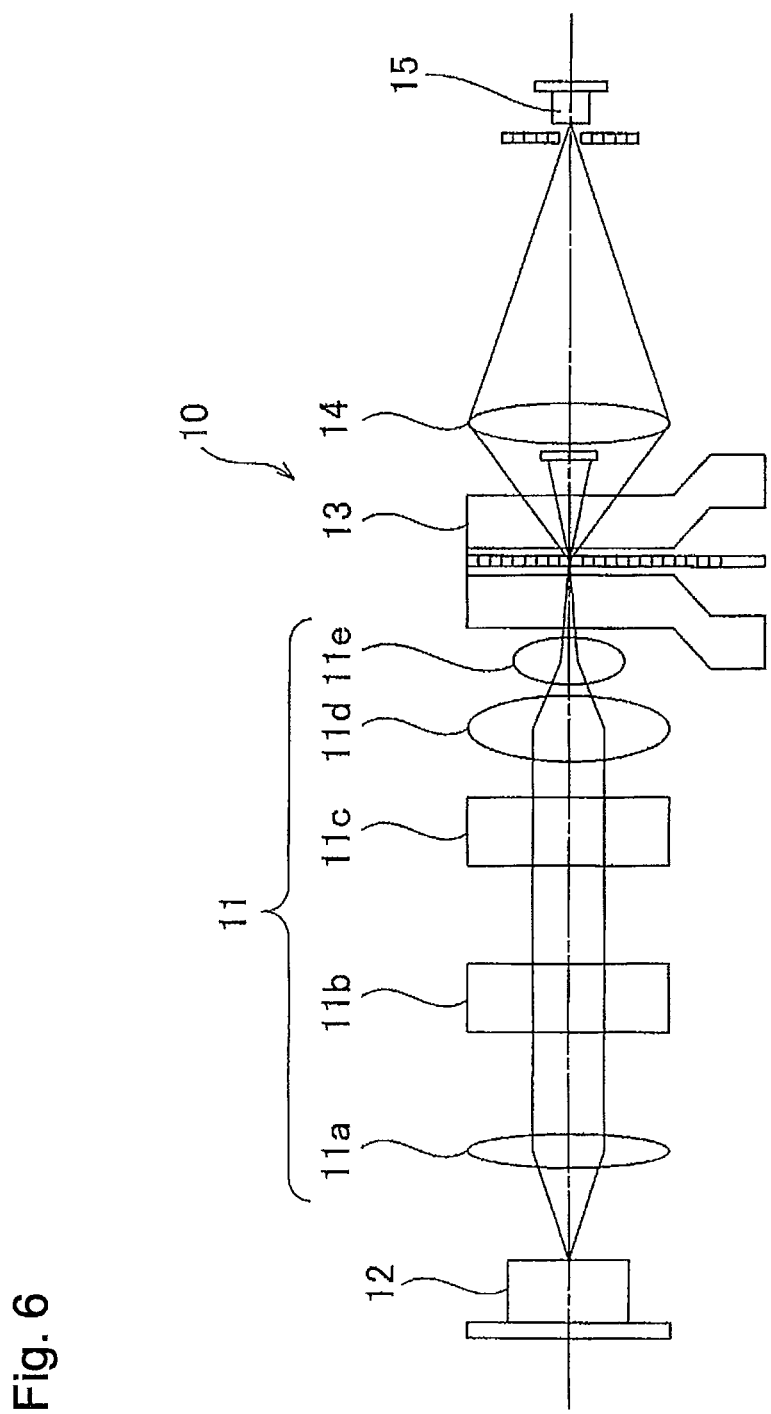
FIG. 6 is a schematic diagram showing an optical system of the flow cytometer shown in FIG. 5.

The primary detection unit 21 has a function of detecting target cells (cervical uterine epithelial cells) in the measurement specimen, the number of and the size of each of, the cells and nuclei therein, and the like. In the first embodiment, the primary detection unit 21 employs a flow cytometer 10 as shown in FIGS. 5 and 6.

The signal processing unit 22 includes a signal processing circuit that performs necessary signal processing on output signals from the primary detection unit 21. The measurement control unit 23 includes a microprocessor 25 and a memory unit 26. The memory unit 26 includes, among others, a RAM, and a ROM having stored therein control programs and data for the primary detection unit 21 and the like.

The microprocessor 25 of the measurement control unit 23 is connected to the data processing apparatus 4 and a microprocessor 36 of the preparation control unit 33 described later, via the I/O interface 24. Accordingly, the microprocessor 25 can transmit and receive various types of data to and from the data processing apparatus 4 and the microprocessor 36 of the preparation control unit 33.

The supplementary detection unit 31 has a function of detecting the number of cells to be measured, contained in a biological specimen. In the first embodiment, the supplementary detection unit 31 also employs the flow cytometer 10 that is substantially the same as that shown in FIGS. 5 and 6. The signal processing unit 32 includes a signal processing circuit that performs necessary signal processing on output signals from the supplementary detection unit 31. The preparation control unit 33 includes the microprocessor 36, a memory unit 37, a sensor driver 38, and a driving unit driver 39. Further, the memory unit 37 includes, among others, a RAM, and a ROM having stored therein control programs and the like for controlling the supplementary detection unit 31, the preparation device unit 35 and the like.

The preparation device unit 35 is configured to include, typically, a sample setting unit 50, a first dispersion unit 51, a sample pipetting unit 52, a separation/substitution unit 53, a container transfer unit 54, a second dispersion unit 55, a liquid removing unit 56, a reaction unit 57, a first reagent adding unit 58a, a second reagent adding unit 58b, a specimen aspirating unit 59, and a container cleaning unit 66.

Figure 3:
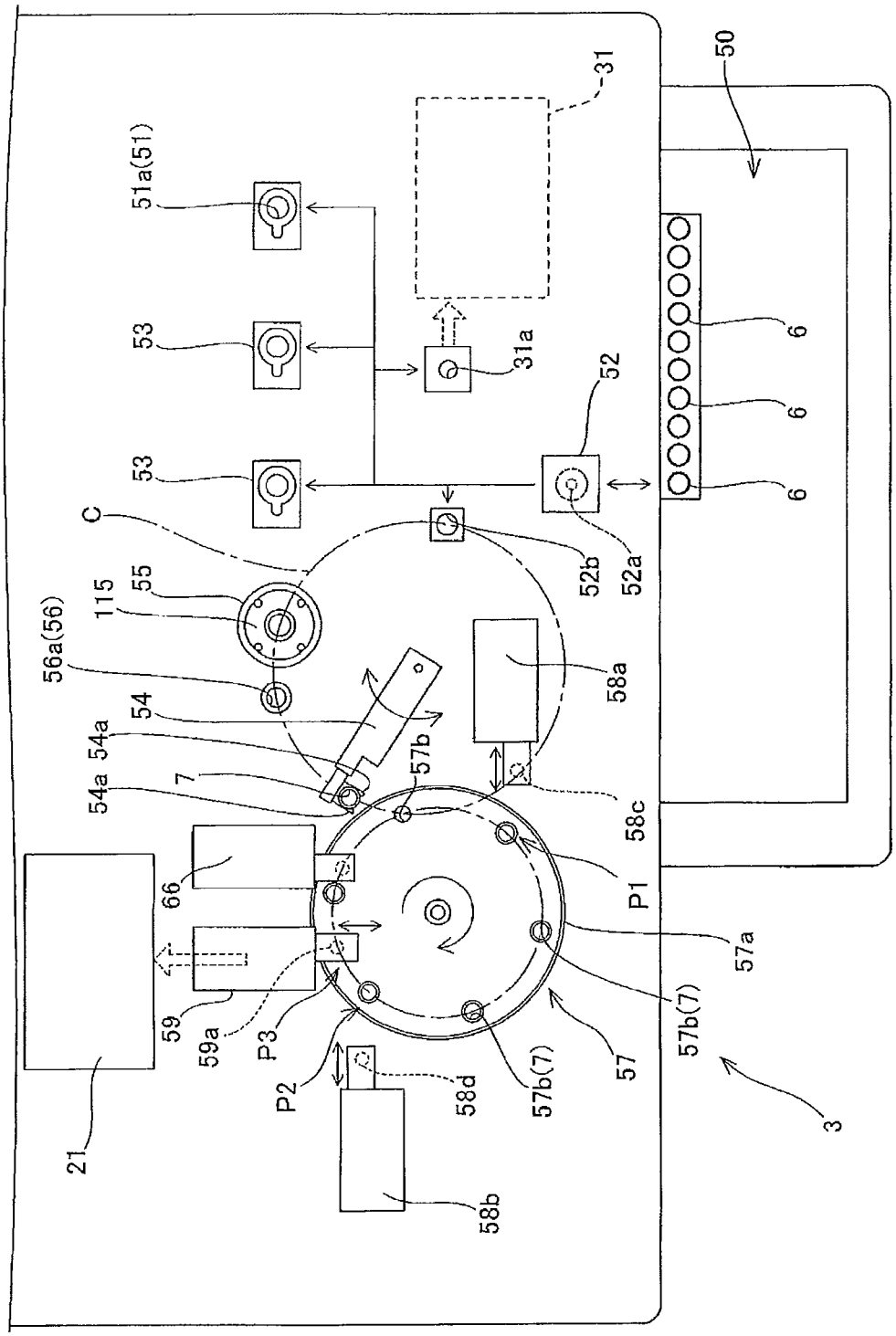
FIG. 3 is a schematic diagram showing an arrangement, seen in a plan view, of components of the measuring apparatus shown in FIG. 2.

FIG. 3 illustrates a component arrangement 3 of the measuring apparatus 2. As shown in FIG. 3, the sample setting unit 50 is for setting thereon a plurality of biological specimen containers 6 each containing a mixed solution of a biological specimen and a preservative solution including methanol as principal component. The sample setting unit 50 has a function of sequentially transporting biological specimen containers 6 set thereon, to an aspiration position at which the sample pipetting unit 52 aspirates a biological specimen.

The first dispersion unit 51 has a function of performing, on a biological specimen, a first dispersion process for dispersing aggregated cells contained in the biological specimen. In the first embodiment, the first dispersion process is a shearing force applying process of applying a shearing force to aggregated cells in order to disperse them. The first dispersion unit 51 includes a specimen holding chamber 51a which can receive a biological specimen, and is configured to mechanically apply a shearing force to aggregated cells in a biological specimen provided in the specimen holding chamber 51a. A configuration of the first dispersion unit 51 will be described later in detail.

The sample pipetting unit 52 has the following functions: transferring a biological specimen in a biological specimen container 6 to the first dispersion unit 51; transferring the biological specimen in the first dispersion unit 51 to the separation/substitution unit 53 which condenses the specimen, and to the supplementary detection unit 31; and supplying a condensed solution in the separation/substitution unit 53 to a measurement specimen container 7. Specifically, the sample pipetting unit 52 is configured to be movable to a position above each of the specimen holding chamber 51a of the first dispersion unit 51, the separation/substitution unit 53, a specimen loading part 31a of the supplementary detection unit 31, a measurement specimen container 7 positioned at a specimen relaying part 52b, and the like. Further, the sample pipetting unit 52 has a pipette 52a which aspirates and discharges a biological specimen. The sample pipetting unit 52 is configured to be able to quantify a biological specimen by means of a sample quantitating unit (not shown; this unit is composed of a quantitative cylinder, a motor that drives a piston in the quantitative cylinder, etc.), and to supply the biological specimen by a predetermined amount to each of the components as described above.

The separation/substitution unit 53 has a function of receiving a mixed solution of a preservative solution and a biological specimen that has been subjected to the first dispersion process in the first dispersion unit 51, and substituting the preservative solution including methanol as principal component, with a diluent. Further, the separation/substitution unit 53 has a function of discriminating between cells to be measured and cells other than those (red blood cells, white blood cells, bacteria, etc.) contained in a biological specimen. Further, the separation/substitution unit 53 has a function of condensing a biological specimen containing cells to be measured (epithelial cells) in order to obtain the number of cells necessary for measurement performed in the primary detection unit 21. Two separation/substitution units 53 are provided for efficient processing. Since the separation/substitution unit 53 can employ the known configuration disclosed in US Patent Application Publication No. 2011/0014685 mentioned above, description of a specific configuration of the separation/substitution unit 53 will be omitted.

The container transfer unit 54 has a function of holding a measurement specimen container 7 which an user has set in the reaction unit 57, between scissors-shaped grippers 54a; and transferring the measurement specimen container 7 to each of the specimen relaying part 52b, the second dispersion unit 55, the liquid removing unit 56, and the reaction unit 57. The container transfer unit 54 is configured to move the grippers 54a along a circular path C about a predetermined rotation center. Further, the container transfer unit 54 is configured to be able to move the grippers 54a in the up-down direction. It should be noted that the specimen relaying part 52b, the second dispersion unit 55, the liquid removing unit 56, and the reaction unit 57 are arranged on this circular path C. This allows the grippers 54a of the container transfer unit 54 to hold and transfer a measurement specimen container 7 which the user has set in the reaction unit 57, to each of the components arranged along the circular path C.

The second dispersion unit 55 has a function of performing a second dispersion process which is different from the first dispersion process, on a biological specimen on which the first dispersion unit 51 has performed the first dispersion process. In the first embodiment, the second dispersion process is an ultrasonic dispersion process of dispersing aggregated cells, by using ultrasonic waves. Specifically, the second dispersion unit 55 is configured to apply ultrasonic vibration to a biological specimen which has been subjected to the first dispersion process in the first dispersion unit 51, followed by the condensation in separation/substitution unit 53, in which the concentration of cells to be measured has been increased. At this time, in the first embodiment, the second dispersion process (ultrasonic dispersion process) is configured to be performed on a biological specimen having an amount smaller than that of the biological specimen on which the first dispersion process has been performed. Accordingly, the second dispersion unit 55 disperses, into single cells, the remaining aggregates of cells even after the first dispersion process. In this manner, in the first embodiment, a cell dispersion unit of the cell analyzer 1 is composed of the first dispersion unit 51 which performs the first dispersion process and the second dispersion unit 55 which performs the second dispersion process. A configuration of the second dispersion unit 55 will be described later in detail.

The liquid removing unit 56 has a function of removing residual liquid from the external surface of a measurement specimen container 7 (drying-out), after the second dispersion unit 55 has performed the second dispersion process. As described later, a measurement specimen container 7 is immersed in a liquid 113 while the second dispersion process is performed (see FIG. 15). The liquid removing unit 56 is configured to supply airflow to the external surface of the measurement specimen container 7 set in a setting port 56a, which has liquid drops thereon, in order to remove the liquid drops from the external surface. This prevents liquid from transferring from the measurement specimen container 7 to a component (e.g. reaction unit 57) around the time of the container's positioning in the component.

The reaction unit 57 has a function of accelerating reactions in a measurement specimen container 7, between a biological specimen and reagents added by the first reagent adding unit 58a and the second reagent adding unit 58b. The reaction unit 57 includes a round rotatable table 57a configured to be rotatable by a driving unit (not shown). A plurality of holders 57b each capable of holding a measurement specimen container 7 therein are provided in an outer periphery portion of the rotatable table 57a. Measurement specimen containers 7 are set in holders 57b by the user. Further, the path of the holders 57b made through rotation of the rotatable table 57a intersects the circular path C of the grippers 54a of the container transfer unit 54 at a predetermined position, and thus, it is configured such that the container transfer unit 54 can set a measurement specimen container 7 in a holder 57b at this intersecting position. Further, the reaction unit 57 has a function of heating each measurement specimen container 7 set in a holder 57b to a predetermined temperature in order to accelerate the reactions between the biological specimen and the reagents.

Each of the first reagent adding unit 58a and the second reagent adding unit 58b has a function of supplying a reagent into a measurement specimen container 7 set in a holder 57b of the reaction unit 57 (the rotatable table 57a). The first reagent adding unit 58a (the second reagent adding unit 58b) is installed at a position near the periphery of the rotatable table 57a and has a supply part 58c (58d) which can extend to a first reagent adding position P1 (second reagent adding position P2) above a measurement specimen container 7 set on the rotatable table 57a. This allows for addition of a predetermined amount of a reagent from the supply part 58c (58d) into a measurement specimen container 7 when the rotatable table 57a transports the measurement specimen container 7 to the first reagent adding position P1 (the second reagent adding position P2).

In the first embodiment, the reagent added by the first reagent adding unit 58a is an RNAse for performing RNA processing on cells, and the reagent added by the second reagent adding unit 58b is a stain solution for performing PI staining. The RNA processing is a process for degrading RNA in cells. This RNA processing allows for measurements specific to DNAs of cell nuclei. Propidium iodide (PI) is used for PI staining, in which PI is a fluorescent stain solution that contains dye. In PI staining, the nucleus in a cell is selectively stained, and thus, fluorescence from the nucleus can be detected. In the first embodiment, it is configured such that addition of the reagents (RNAse and stain solution) is performed after the first dispersion process and the second dispersion process have been performed.

The specimen aspirating unit 59 has a function of aspirating the measurement specimen in a measurement specimen container 7 set in the reaction unit 57 (the rotatable table 57a) and transferring the measurement specimen to the primary detection unit 21 (see FIG. 2). The specimen aspirating unit 59 is installed at a position near the periphery of the rotatable table 57a, and has a pipette 59a movable to an aspiration position P3 above a measurement specimen container 7 set in the rotatable table 57a. Accordingly, when a measurement specimen container 7 has been transported to the aspiration position P3 by the rotatable table 57a, the specimen aspirating unit 59 can aspirate the measurement specimen in the measurement specimen container 7. The specimen aspirating unit 59 is connected to a flow cell 13 described later (see FIGS. 5 and 6) of the primary detection unit 21 via a flow channel (not shown), and is configured to be able to supply the measurement specimen aspirated by the pipette 59a to the flow cell 13 of the primary detection unit 21. It should be noted that, in the first embodiment, as described later, the biological specimen is aspirated by the specimen aspirating unit 59 after the processes by the first reagent adding unit 58a and the second reagent adding unit 58b, without any other process interposed therebetween. Therefore, it is configured such that detection by the primary detection unit 21 is performed immediately after the processes by the first reagent adding unit 58a and the second reagent adding unit 58b have been completed.

The container cleaning unit 66 has a function of cleaning the inside of a measurement specimen container 7 after its measurement specimen has been supplied by the specimen aspirating unit 59 to the primary detection unit 21. The container cleaning unit 66 is configured to clean the inside of a measurement specimen container 7 by discharging a cleaning fluid into the measurement specimen container 7 held in a holder 57b of the rotatable table 57a. Accordingly, when the same measurement specimen container 7 is used in a measurement process thereafter, contamination to another biological specimen can be suppressed.

As shown in FIG. 2, the microprocessor 36 of the preparation control unit 33 is connected to the microprocessor 25 of the measurement control unit 23 via the I/O interface 24. Accordingly, the microprocessor 36 can transmit and receive various types of data to and from the microprocessor 25 of the measurement control unit 23.

Further, the microprocessor 36 of the preparation control unit 33 is connected, via the sensor driver 38 or the driving unit driver 39, to sensors and driving motors of the components (the sample setting unit 50, the first dispersion unit 51, the sample pipetting unit 52, the separation/substitution unit 53, the container transfer unit 54, the second dispersion unit 55, the liquid removing unit 56, the reaction unit 57, the first reagent adding unit 58a, the second reagent adding unit 58b, and the specimen aspirating unit 59) of the preparation device unit 35. Accordingly, based on detection signals from the sensors, the microprocessor 36 executes control programs to control operations of the driving motors.

Figure 4:
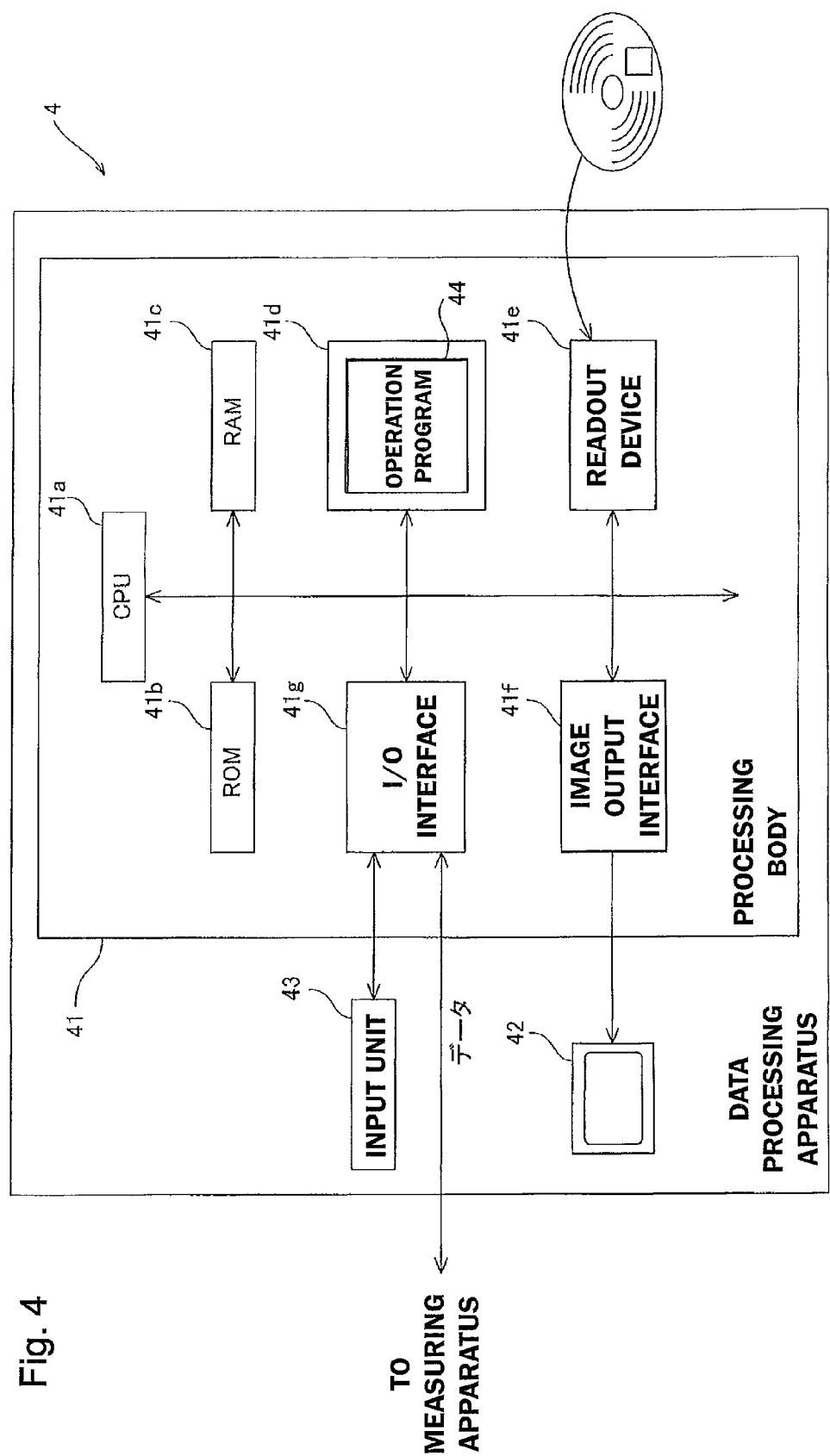
FIG. 4 is a block diagram showing a configuration of a data processing apparatus of the cell analyzer shown in FIG. 1.

As shown in FIG. 4, the data processing apparatus 4 in the first embodiment is composed of a personal computer such as a notebook PC (or a desk top PC), and is configured to include, typically, a processing body 41, a display unit 42, and an input unit 43.

The processing body 41 includes a CPU 41a, a ROM 41b, a RAM 41c, a hard disk 41d, a readout device 41e, an image output interface 41f, and an input/output interface 41g. These components are communicably connected to each other by an internal bus.

The hard disk 41d has installed therein various types of programs such as an operating system and application programs, and in addition, an operation program 44 for performing: transmission of operation instructions to the measurement control unit 23 (see FIG. 2) and the preparation control unit 33 (see FIG. 2); reception and analysis processing of results of measurements performed in the measuring apparatus 2 (see FIG. 1); and display of processed analysis results. The operation program 44 runs on the operating system.

The input unit 43 composed of a keyboard and a mouse is connected to the input/output interface 41g. Further, the input/output interface 41g is also connected to the I/O interface 24 (see FIG. 2) of the measuring apparatus 2 (see FIG. 2). Accordingly, the measuring apparatus 2 and the data processing apparatus 4 can transmit and receive data therebetween.

Next, the flow cytometer 10 forming the primary detection unit 21 of the measuring apparatus 2 will be described. As shown in FIG. 5, a lens system 11 of the flow cytometer 10 has a function of condensing a laser beam from a light source, i.e. semiconductor laser 12, on a measurement specimen flowing in the flow cell 13 which allows a biological specimen to pass therethrough. A condenser lens 14 has a function of condensing forward scattered light from a cell in the measurement specimen, onto a scattered light detector including a photodiode 15.

Specifically, as shown in FIG. 6, the lens system 11 includes, from the semiconductor laser 12 side (left in FIG. 6), a collimator lens 11a, a cylindrical lens system (planoconvex cylindrical lens 11b+biconcave cylindrical lens 11c), and a condenser lens system (condenser lens 11d+condenser lens 11e), in this order.

As shown in FIG. 5, a condenser lens 16 for side light has a function of condensing side scattered light and side fluorescence from a cell to be measured and the nucleus in this cell onto a dichroic mirror 17. The dichroic mirror 17 is configured to reflect side scattered light to a photomultiplier 18 (photo-multiplier tube) and is also configured to pass side fluorescence therethrough toward a photomultiplier 19 (photo-multiplier tube). These lights reflect properties of a cell and/or a nucleus in the measurement specimen.

Then, the photodiode 15, and the photomultipliers 18 and 19 convert received light signals into electric signals to output them as a forward scattered light signal (FSC), a side scattered light signal (SSC), and a side fluorescence signal (SFL), respectively. These output signals are amplified by a preamplifier (not shown), to be sent to the signal processing unit 22 of the measuring apparatus 2 (see FIG. 2). Each of the FSC, SSC, and SFL signals processed in the signal processing unit 22 of the measuring apparatus 2 is transmitted by the microprocessor 25 via the I/O interface 24 to the data processing apparatus 4.

The CPU 41a of the data processing apparatus 4 obtains characteristics parameters such as forward scattered light intensity, side fluorescence intensity and the like based on the FSC, SSC, and SFL signals, by executing the operation program 44, and generates frequency distribution data for analyzing cells and nuclei based on these characteristics parameters. Then, the CPU 41a performs a distinction process of particles in the measurement specimen, and determines whether the cells to be measured (epithelial cells) are abnormal, specifically, whether they are cancerous cells (atypical cells), based on this frequency distribution data.

Detailed description of the supplementary detection unit 31 will be omitted herein since it employs the flow cytometer 10 having substantially the same configuration as that of the primary detection unit 21 as described above. It should be noted that the supplementary detection unit 31 performs preliminary measurement of the concentration of the cells to be measured, before the primary detection unit 21 performs a main measurement. Therefore, it is sufficient if the supplementary detection unit 31 can output signals for counting the number of the cells, that is, if the supplementary detection unit 31 can obtain forward scattered light signals (FSC).

Figure 7:
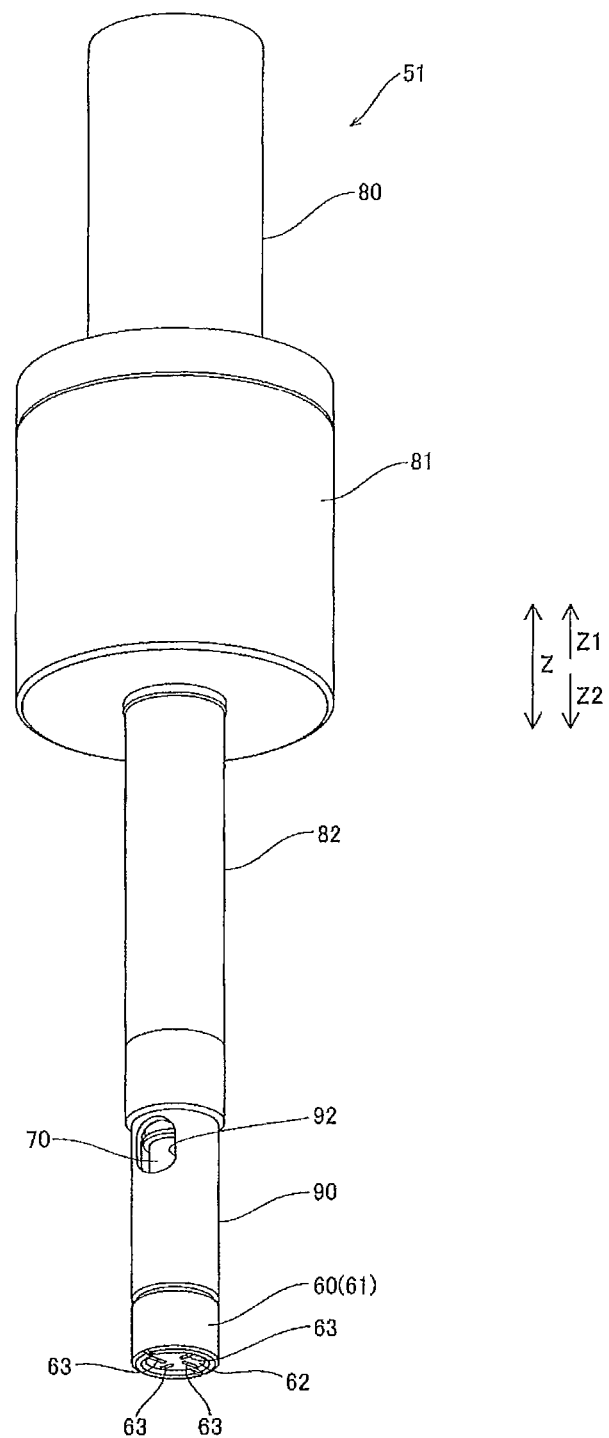
FIG. 7 is a perspective view showing an overall structure of a first dispersion unit of the measuring apparatus shown in FIG. 3.
Figure 8:
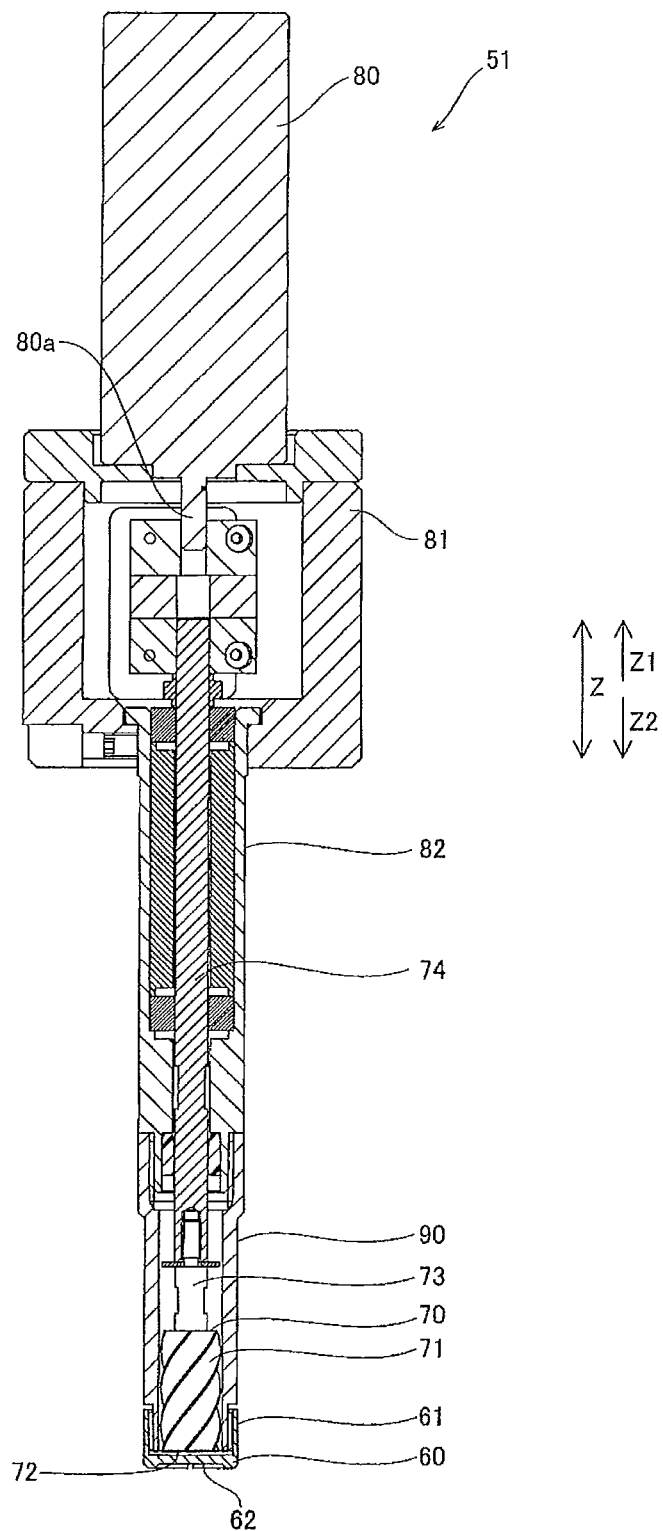
FIG. 8 is a longitudinal sectional view of the first dispersion unit shown in FIG. 7.

Next, a specific configuration of the first dispersion unit 51 will be described. As shown in FIGS. 7 and 8, the first dispersion unit 51 includes an apertured member 60, a rotor 70, and a motor 80 which drives the rotor 70 to rotate. A pipe 90 having a function of guiding a flow of the biological specimen is arranged outside the rotor 70, and the apertured member 60 is attached to an opening at an end of the pipe 90. By rotating the rotor 70 with these inserted in the specimen holding chamber 51a (see FIG. 14), aggregated cells contained in the biological specimen in the specimen holding chamber 51a are dispersed into single cells.

Figure 9:
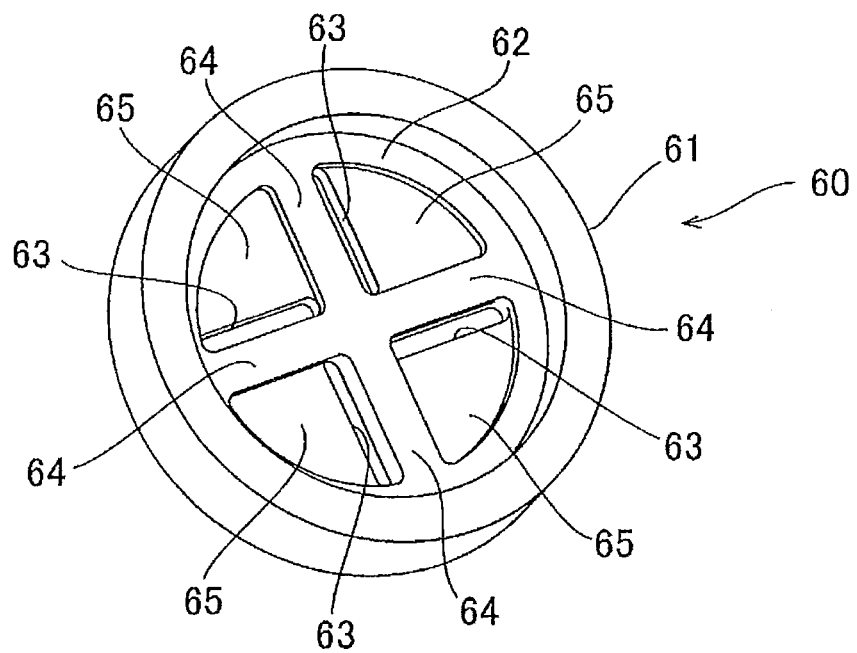
FIG. 9 is a perspective view showing an apertured member of the first dispersion unit shown in FIG. 7.
Figure 10:
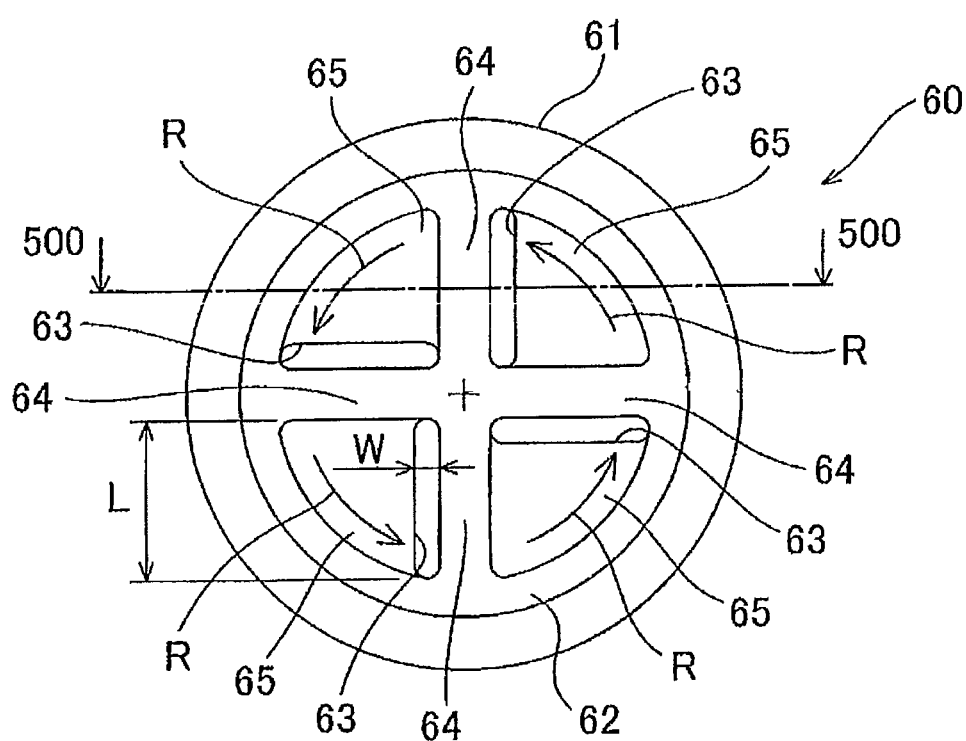
FIG. 10 is a top view of the apertured member shown in FIG. 9.
Figure 11:
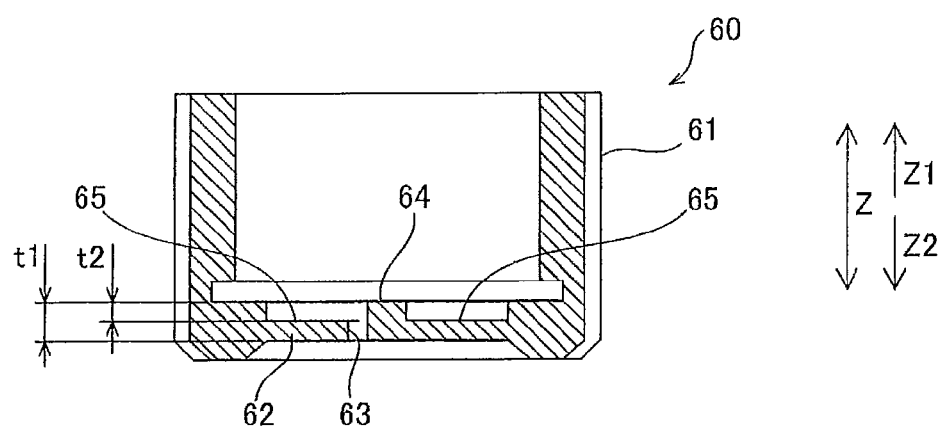
FIG. 11 is a cross-sectional view of the apertured member cut along the line 500-500 in FIG. 10.

As shown in FIGS. 9 to 11, the apertured member 60 is made of stainless steel in consideration of chemical resistance and strength, and a tubular part 61 having a cylindrical shape is integrally formed with a bottom 62. The bottom 62 is provided so as to block the lower end of the tubular part 61 and has four apertures 63 therein. The apertured member 60 is attached to the opening at the end of the pipe 90. As shown in FIGS. 10 and 11, the bottom 62 is formed in a round shape when seen in a plan view, and has four apertures 63 extending from the upper face (internal surface) to the lower face (external surface) thereof. Each of these apertures 63 has a size that allows aggregated cells (the size: about not less than 100 µm and about not greater than 500 µm) to pass therethrough.

Four projecting parts 64, which extend in a direction (radial direction) orthogonal to the rotational direction (arrow R direction) of the rotor 70 when seen in a plan view, and which project toward the rotor 70 side (upward), are formed on the upper face of the bottom 62. Further, four liquid retaining parts 65 composed of recesses defined by these projecting parts 64 are formed in the upper face of the bottom 62. As shown in FIG. 11, the thickness of the bottom 62 (each projecting part 64) is t1 (about 1 mm), and the depth of each liquid retaining part 65 is t2 (about 0.5 mm).

As shown in FIG. 10, the four apertures 63 of the bottom 62 are arranged in the four liquid retaining parts 65, respectively. Further, each aperture 63 has an elongated shape having a width W (about 0.5 mm) and a length L (about 3.25 mm). Further, the aperture 63 is formed so as to extend in a direction orthogonal to the direction of the arrow R (rotational direction of the rotor 70). More specifically, the aperture 63 is arranged inside the fan-shaped liquid retaining part 65, along the edge in the rotor 70's rotational direction (arrow R direction) side of the liquid retaining part 65, so as to extend parallel to and adjacent to the corresponding projecting part 64. Further, the aperture 63 is formed so as to extend from the inner end in the radial direction of the fan-shaped liquid retaining part 65 to the outer end in the radial direction thereof.

Figure 12:
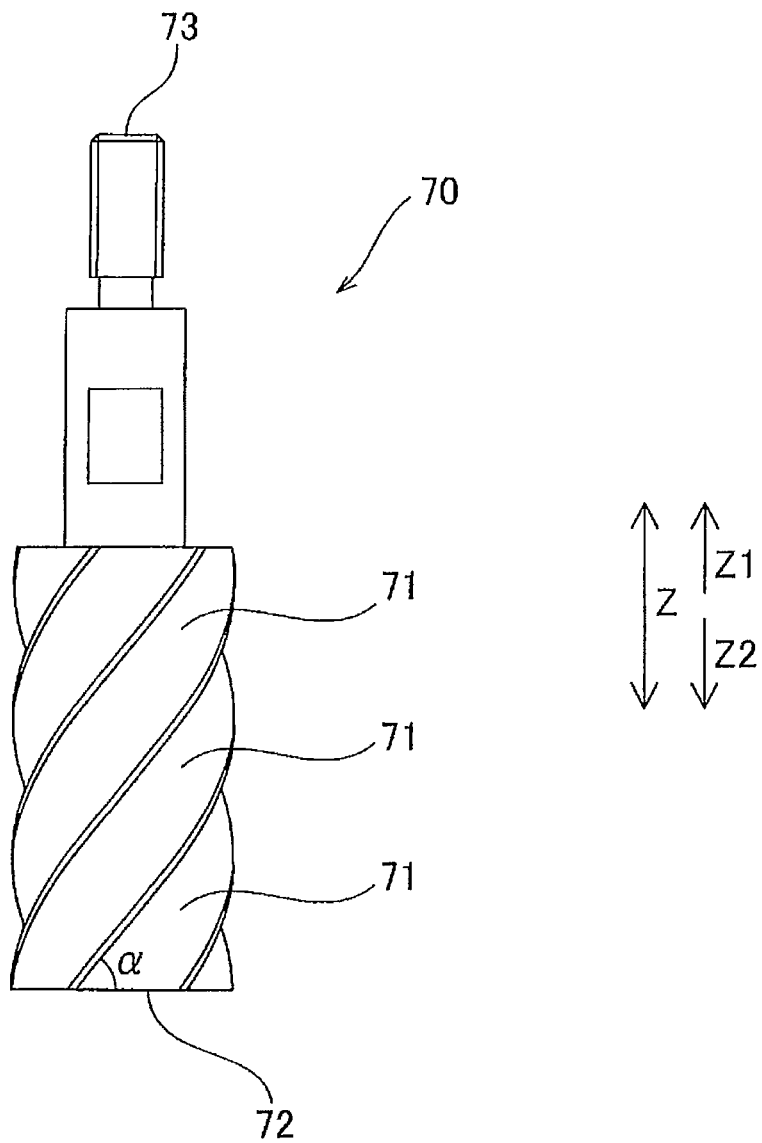
FIG. 12 is a side view showing a rotor of the first dispersion unit shown in FIG. 7.
Figure 13:
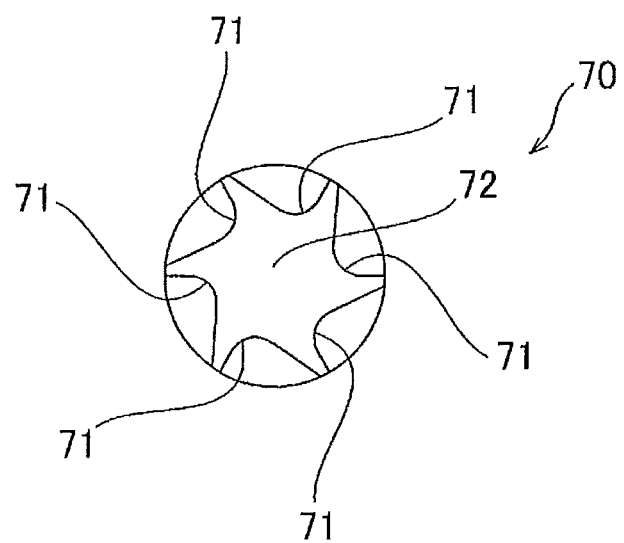
FIG. 13 is a bottom view of the rotor shown in FIG. 12.

As shown in FIG. 8, the rotor 70 is made of stainless steel in consideration of chemical resistance and strength, as in the case of the bottom 62, and is arranged inside the pipe 90. A spiral groove 71 is formed on the outer periphery of the rotor 70, as shown in FIGS. 12 and 13. The groove 71 is formed to have a lead angle alpha (about 40 degrees). Further, the groove 71 is provided such that the rotation of the groove 71 sends the biological specimen downward (arrow Z2 direction) where the apertured member 60 is arranged, when the rotor 70 is rotated in the arrow R direction (see FIG. 10). This allows the biological specimen to be supplied toward the bottom 62 below (to apply a downward propelling force to the biological specimen) when the rotor 70 is rotated around the axial direction by the motor 80 (in arrow R direction). Further, a lower end face 72 of the rotor 70 is formed to be flat.

Figure 14:
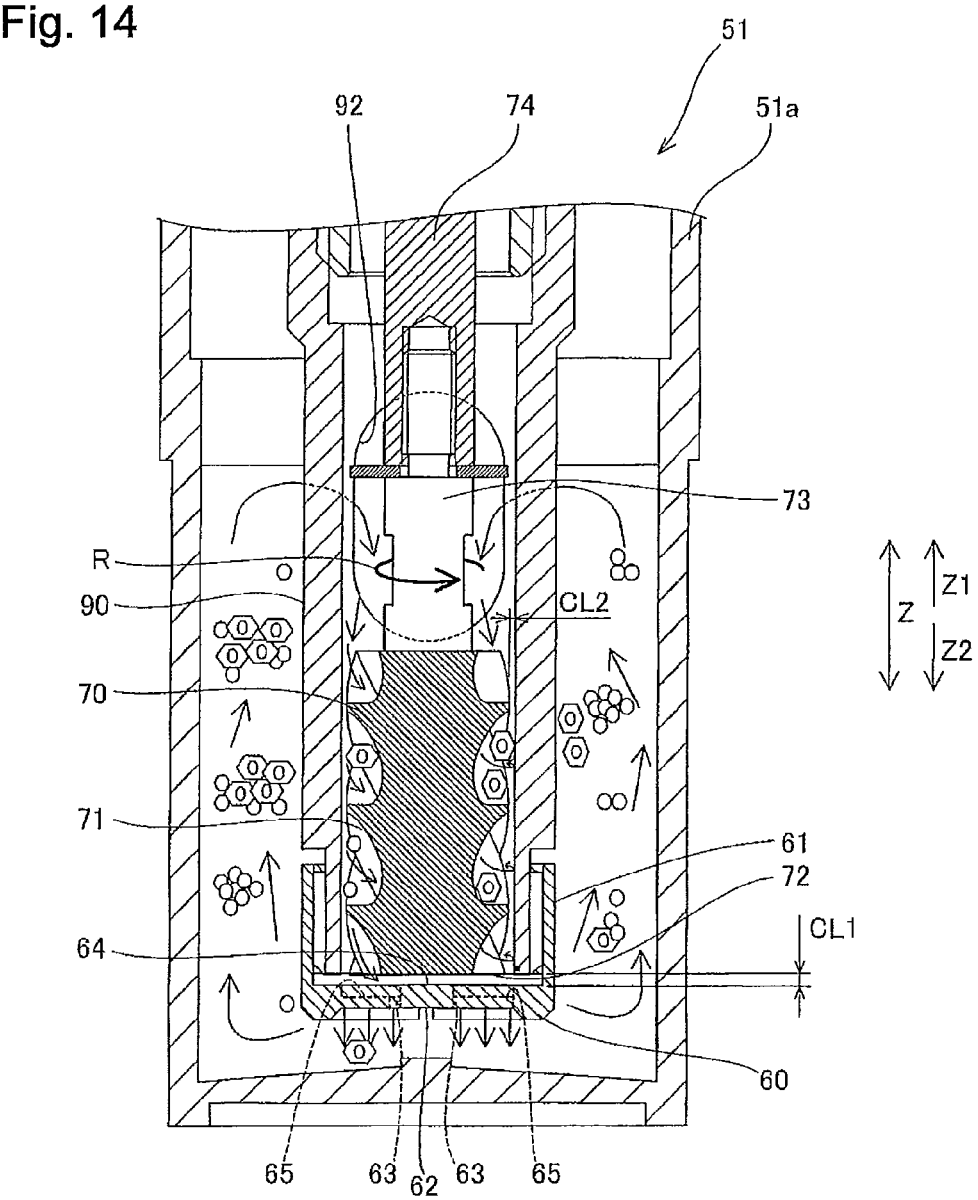
FIG. 14 is a schematic diagram for explaining operations performed by the first dispersion unit shown in FIG. 7.

As shown in FIG. 14, it is configured such that the lower end face 72 of the rotor 70 is distanced from the upper face of the bottom 62 (upper face of the projecting part 64) of the apertured member 60 attached to the lower end of the pipe 90, by a predetermined interval CL1. The interval CL1 has a size that does not allow aggregated cells (not less than 100 µm) to pass therethrough, and that allows single cells (average 60 µm) to pass therethrough. Thus, the interval CL1 is set to be in a range of 30 to 80 µm so as to have substantially the same size as that (average 60 µm) of an epithelial cell (single cell) of the uterine cervix which is to be measured. In the first embodiment, the interval CL1 is about 50 µm. It should be noted that, in FIG. 14, the interval CL1 is exaggerated for the purpose of illustration.

Here, since aggregated cells have a size exceeding 100 µm, a shearing force can be effectively applied to aggregated cells, by setting the interval CL1 to about 50 µm. As described above, the first dispersion unit 51 is configured to disperse aggregated cells between each projecting part 64 of the apertured member 60 and the lower end face 72 of the rotor 70, through the motor 80-driven rotation of the rotor 70. The reason why the interval CL1 is set to 30 to 80 µm is that if it is less than 30 µm, cells may be crushed, and if it is greater than 80 µm, the dispersion force applied to aggregated cells may be reduced.

As shown in FIG. 8, an upper end 73 of the rotor 70 is connected to an output shaft 80a of the motor 80 via a rotation shaft 74. Accordingly, a driving force (rotary force) of the motor 80 is transmitted to the rotor 70. The motor 80 is attached to the upper face of a support member 81. A tubular body 82 is attached to a lower part of the support member 81 so as to extend downward. The rotation shaft 74 is rotatably supported inside the tubular body 82.

The pipe 90 is formed of a circular pipe made of stainless steel having an internal diameter that allows the rotor 70 to be accommodated therein. The upper end of the pipe 90 is connected to the tubular body 82 having the rotation shaft 74 inserted therein. The rotor 70 attached to the rotation shaft 74 is arranged such that its lateral side and lower side are surrounded by the pipe 90 and the apertured member 60. It should be noted that, as shown in FIG. 14, the outer periphery of the rotor 70 with the groove 71 formed thereon is slightly distanced from the inner periphery surface of the pipe 90 by an interval CL2 (about 0.3 mm).

Two openings 92 (see FIGS. 7 and 14) each having a long hole shape are formed on the side wall of the pipe 90, at positions slightly higher than the rotor 70. The two openings 92 are formed at positions opposite to each other relative to the axis of the pipe 90. As shown in FIG. 14, the biological specimen outside the pipe 90 is introduced through each opening 92 as an inlet port into the pipe 90, and is moved from the inlet port, through the pipe 90, to a lower part (in the arrow Z2 direction), by the rotor 70. Then, the biological specimen flows out of the pipe 90 through each aperture 63, as an outlet port, of the apertured member 60 at the lower end, and flows into the opening 92 (inlet port) again. In this manner, a circulating flow is formed in which cells in the biological specimen circulate, from the inlet port (opening 92), to the inside of the pipe 90, then to the outlet port (aperture 63), then to the outside of the pipe 90, and then into the inlet port (opening 92).

Figure 15:
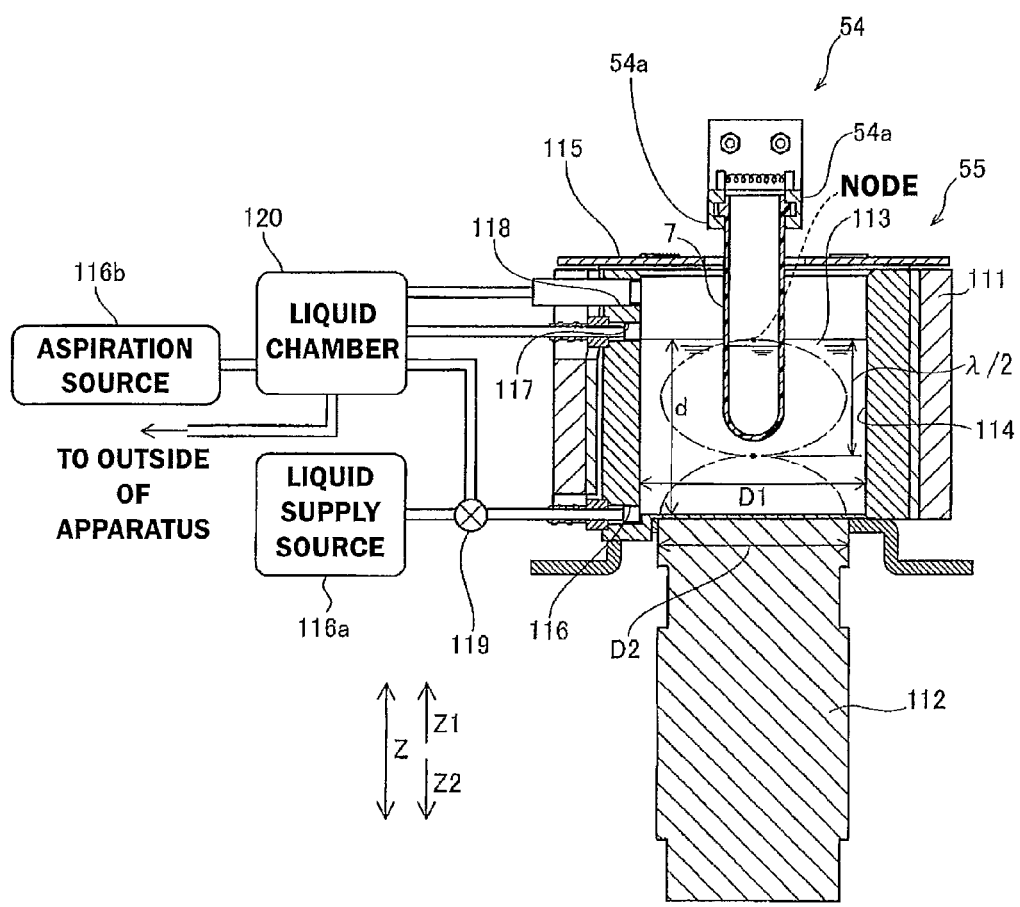
FIG. 15 is a cross-sectional view schematically showing an overall structure of a second dispersion unit of the measuring apparatus shown in FIG. 3.

Next, a specific configuration of the second dispersion unit 55 will be described. As shown in FIG. 15, the second dispersion unit 55 includes a liquid holding chamber 111 which receives the liquid 113 such as water, and an ultrasonic transducer 112 which applies ultrasonic vibration to the biological specimen in a measurement specimen container 7 through the liquid 113.

The liquid holding chamber 111 has a recess 114 in the middle which receives the liquid 113, and is formed in a substantially cylindrical shape. At an opening at the upper end of the recess 114, there is provided a lid 115 in which a round hole of a size that allows a measurement specimen container 7 to be inserted therethrough is formed. It is configured such that the lid 115 prevents the liquid 113 from scattering to the outside during ultrasonic vibration.

The ultrasonic transducer 112 has a columnar shape and is arranged to a lower side of the liquid holding chamber 111. As the ultrasonic transducer 112, for example, a known ultrasonic transducer used for cleaning parts can be used. An internal diameter D1 of the cylindrical liquid holding chamber 111 is greater than an outer diameter D2 of the columnar ultrasonic transducer 112, by about several millimeters (e.g., about 5 mm to 6 mm). By making the size of the area of the liquid 113 (the internal diameter D1 of the liquid holding chamber 111) to which ultrasonic waves are applied greater than the outer diameter D2 of the ultrasonic transducer 112, the ultrasonic vibration can be efficiently transmitted to the liquid 113.

The peripheral wall of the substantially-cylindrical liquid holding chamber 111 is provided with a liquid communication hole 116, an upper outlet hole 117, and an overflow channel (hole) 118 upwardly in this order. The liquid communication hole 116, the upper outlet hole 117, and the overflow channel 118 are communicated with the outside of the liquid holding chamber 111.

The liquid communication hole 116 is formed at a position near the bottom face of the recess 114, and is provided for supplying/discharging the liquid 113 to/from the liquid holding chamber 111 (the recess 114). The liquid communication hole 116 is communicated with a liquid supply source 116a, and a liquid chamber 120 connected to an aspiration source 116b, via a flow channel switching valve 119. When the liquid 113 is supplied, the flow channel switching valve 119 causes the liquid supply source 116a to be communicated with the liquid communication hole 116 (the recess 114), and the liquid 113 is supplied from the liquid supply source 116a to the recess 114. On the other hand, when the liquid 113 is discharged, the flow channel switching valve 119 causes the liquid chamber 120 to be communicated with the liquid communication hole 116 (the recess 114), and the liquid 113 in the recess 114 is aspirated into the liquid chamber 120 by the aspiration source 116b. The liquid aspirated by the aspiration source 116b is discharged from the liquid chamber 120, to the outside of the apparatus.

The upper outlet hole 117 is communicated with the liquid chamber 120, and has a function of discharging the liquid 113 in the recess 114. Thus, by means of the upper outlet hole 117, a depth (upper limit position) d of the liquid 113 in the recess 114 is determined. In the first embodiment, in order to effectively generate ultrasonic vibration, the depth d (height of the lower end of the upper outlet hole 117 from the bottom face of the recess 114) is set such that a node of ultrasonic waves generated by the ultrasonic transducer 112 is positioned on the surface of the liquid 113 received in the recess 114.

Thus, in the first embodiment, while the measurement specimen container 7 is inserted in the liquid holding chamber 111 by a predetermined distance and immersed in the liquid 113, a predetermined amount of the liquid 113 is supplied from the liquid communication hole 116 into the recess 114. Then, the aspiration source 116b is driven by the preparation control unit 33 for a predetermined time period, to discharge (aspirate) an excessive amount of the liquid 113 in the recess 114, from the upper outlet hole 117 into the liquid chamber 120. At this time, the flow channel between the liquid chamber 120 and the liquid supply source 116a is closed by the flow channel switching valve 119. Accordingly, since the height level of the upper outlet hole 117 has been set to be the level (the depth d) of the node of ultrasonic waves generated by the ultrasonic transducer 112, the level of the surface of the liquid 113 is adjusted to be the level (the depth d) of the node of the ultrasonic waves, when the liquid 113 is aspirated from the upper outlet hole 117 for a predetermined time period. The "predetermined time period" for aspirating the liquid 113 may be set to a time period obtained by adding several seconds to a time period calculated based on the supplied amount of the liquid 113 and the aspiration capability of the aspiration source 116b. Even when the aspiration is performed for a longer time period than the calculated time period, the liquid 113 existing lower than the upper outlet hole 117 is not discharged, which causes no trouble in controlling the liquid surface level.

In the second dispersion process performed by the second dispersion unit 55, the measurement specimen container 7 is immersed in the liquid 113 in the liquid holding chamber 111, while being griped by the grippers 54a of the container transfer unit 54. At this time, a lowered position of the container transfer unit 54 (the grippers 54a) is set such that the surface of the liquid in the measurement specimen container 7 is positioned lower than the surface of the liquid 113. When the surface of the liquid in the measurement specimen container 7 is positioned higher than the surface of the liquid 113, ultrasonic waves cannot be effectively transmitted to the liquid in the measurement specimen container 7. This makes it difficult to improve dispersion efficiency for aggregated cells in the biological specimen. In the first embodiment, the surface of the liquid in the measurement specimen container 7 is preferably positioned lower than the surface of the liquid 113 in the recess 114, by about 1 mm to 2 mm.

Here, as shown in FIG. 15, the ultrasonic vibration has significantly high vibration amplitude within a range of $\lambda/2$ between nodes (the lambda ($\lambda$) is the wavelength of the ultrasonic vibration). Therefore, when the liquid in the measurement specimen container 7 is positioned so as to be included in the range of $\lambda/2$, with the measurement specimen container 7 inserted in the recess 114 from above, the ultrasonic waves can be effectively transmitted to the liquid in the measurement specimen container 7. The $\lambda/2$ is about is 28.8 mm when the frequency of the ultrasonic vibration is about 25 kHz, about 18.8 mm when the frequency is about 40 kHz, and about 10 mm when the frequency is about 75 kHz. Therefore, in order to effectively transmit ultrasonic waves to the liquid in the measurement specimen container 7, the height of the surface of the liquid in the measurement specimen container 7 (that is, the amount of the liquid in the measurement specimen container 7) needs to be within the height range of $\lambda/2$. In the first embodiment, by increasing the concentration of (condensing) the cells to be measured in the biological specimen by means of the separation/substitution unit 53, it is possible to reduce the amount of the biological specimen contained in the measurement specimen container 7, while ensuring the number of cells necessary for measurement performed by the primary detection unit 21. As a result, since the height of the surface of the liquid in the measurement specimen container 7 can be made to be within the height range of $\lambda/2$, ultrasonic waves can be effectively transmitted to the liquid in the measurement specimen container 7. Although the frequency of the ultrasonic vibration generated by the ultrasonic transducer 112 is not limited in particular, it is preferably not less than 20 kHz, and more preferably, 20 kHz to 75 kHz, in terms of the liquid amount contained in the measurement specimen container 7 during the second dispersion process and efficient transmission of the ultrasonic vibration.

The overflow channel 118 prevents the liquid 113 from overflowing from the recess 114 even when the liquid 113 is excessively supplied from the liquid supply source 116a for some reason. The overflow channel 118 is provided near an upper end portion of the liquid holding chamber 111 (the recess 114) and is communicated with the liquid chamber 120. When the liquid 113 is excessively supplied to exceed the position of the upper outlet hole 117, and also when the measurement specimen container 7 is excessively inserted into the recess 114, the liquid 113 is discharged from the overflow channel 118 into the liquid chamber 120 without overflowing.

Although the measurement specimen container 7 can be made of a synthetic resin or metal such as stainless steel, it is preferably made of a material having an acoustic impedance substantially equivalent to that of the liquid 113 received in the recess 114. For example, when water is received in the recess 114, the measurement specimen container 7 is preferably made of polypropylene or polyethylene. By making the property (acoustic impedance) of the liquid 113 substantially equivalent to that of the measurement specimen container 7, which exists between the ultrasonic transducer 112 and the biological specimen and which transmits vibration, the ultrasonic vibration can be efficiently transmitted to the biological specimen.

Further, in terms of improving the dispersion effect on aggregated cells, the inner periphery surface of the measurement specimen container 7 preferably has a certain degree of roughness. Specifically, the surface roughness of the inner periphery surface of the measurement specimen container 7 is preferably about 1 to 30 µm, for example.

Next, with reference to FIGS. 2, 3, 5, 8, 9 and 11, and FIGS. 14 to 16, analysis operations performed by the cell analyzer 1 according to the first embodiment will be described. It should be noted that operation control of the primary detection unit 21 and the signal processing unit 22 of the measuring apparatus 2 is performed by the measurement control unit 23 (the microprocessor 25), and operation control of the supplementary detection unit 31, the signal processing unit 32, and the preparation device unit 35 of the measuring apparatus 2 is performed by the preparation control unit 33 (the microprocessor 36). Control of the data processing apparatus 4 is performed by the processing body 41 (the CPU 41a).

Figure 16:
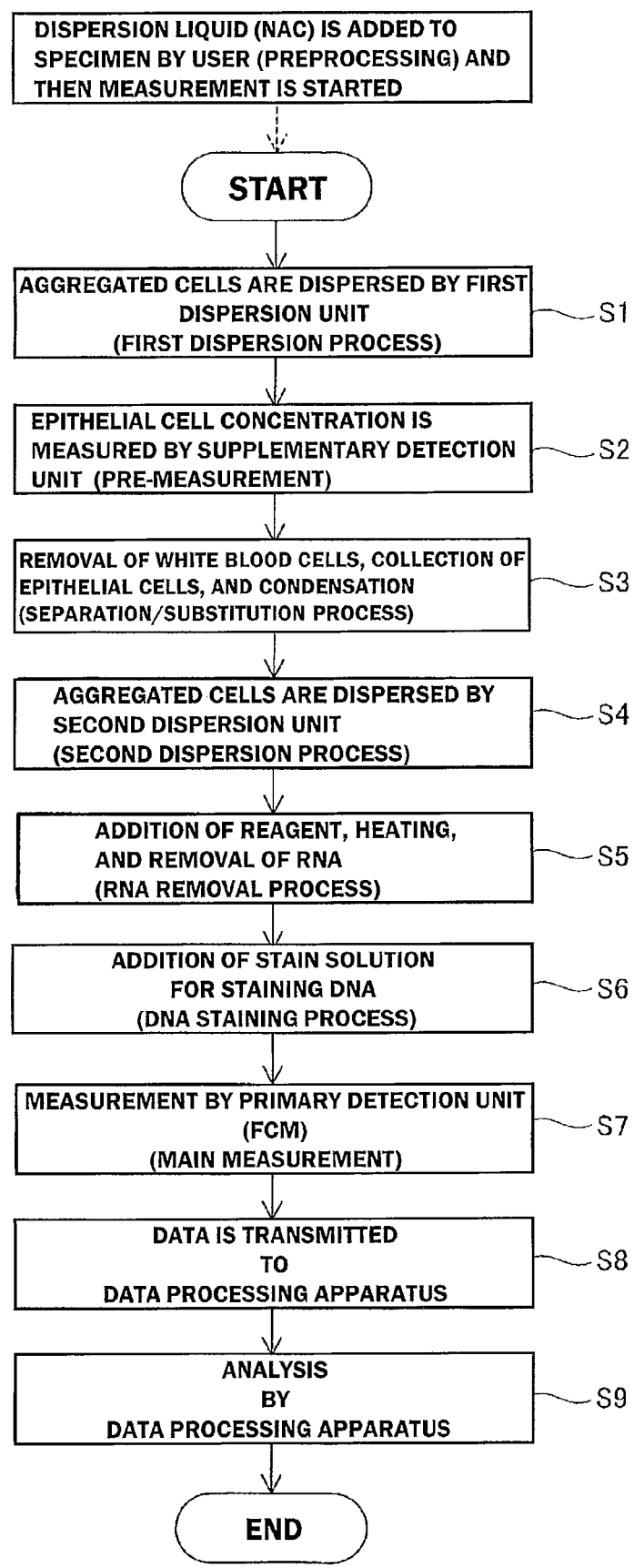
FIG. 16 is a flow chart for explaining analysis operation performed by the cell analyzer according to the first embodiment of the present invention.

As shown in FIG. 16, an user of the cell analyzer 1 performs a preprocessing prior to analysis using the analyzer, and the preprocessing includes, e.g. addition of N-acetyl-L-cysteine (NAC) as a dispersion liquid to a biological specimen. Then, the user sets, in the sample setting unit 50 (see FIG. 3), a biological specimen container 6 containing the biological specimen and the preservative solution including alcohol as principal component, and analysis by the cell analyzer 1 is started.

As the initial step in the analysis, in step S1 in FIG. 16, the first dispersion unit 51 performs a dispersion process (first dispersion process) of aggregated cells in the biological specimen. Specifically, as shown in FIG. 3, the sample pipetting unit 52 in the sample setting unit 50 aspirates the mixed solution in the biological specimen container 6 containing the biological specimen and the preservative solution including alcohol as principal component. Then, the sample pipetting unit 52 moves above the specimen holding chamber 51a of the first dispersion unit 51, and supplies the mixed solution into the specimen holding chamber 51a. Then, the mixed solution in the specimen holding chamber 51a is dispersed in the first dispersion unit 51.

The first dispersion process is performed by the first dispersion unit 51 as follows.

As shown in FIG. 14, first, when the motor 80 (see FIG. 8) is driven to rotate by the preparation control unit 33 (see FIG. 2), the rotation of the motor 80 causes the rotation shaft 74 and the rotor 70 connected to the end of the rotation shaft 74 to rotate about the axis in the arrow R direction. At this time, the rotation of the groove 71 provided on the outer periphery of the rotor 70 sends the biological specimen in the groove 71 (between the lower end face 72 of the rotor 70 and the bottom 62), toward the bottom 62 in lower position. In the first embodiment, the number of rotation of the motor 80 is about 10000 rpm, and the rotation (dispersion of cells) is continuously performed for about 60 seconds.

The biological specimen sent to the bottom 62 flows into each liquid retaining part 65 (see FIG. 9), a recess defined by the projecting parts 64, and is temporarily pooled (retained) in the liquid retaining part 65. At this time, the lower end face 72 of the rotor 70 rotating in the arrow R direction exists above (arrow Z1 direction) the biological specimen that has flowed into the liquid retaining part 65. Accordingly, the biological specimen is moved in the arrow R direction in the liquid retaining part 65. The flow in the arrow R direction of the biological specimen in the liquid retaining part 65 is blocked by a wall surface of a corresponding projecting part 64 (see FIG. 11) defining the liquid retaining part 65. Accordingly, the flow of the biological specimen in the arrow R direction branches into a flow of the biological specimen that moves downward (outside) through the aperture 63 formed at the end in the arrow R direction, and a flow of the biological specimen that moves upward along the wall surface of the projecting part 64 to flow beyond the projecting part 64.

The flow of the biological specimen that moves downward (outside) through the aperture 63 flows (spouts) to the outside of the bottom 62 and is drawn into the inside of the pipe 90 through the openings 92 on the peripheral wall the pipe 90 by the rotation of the rotor 70. As a result, a circulating flow is formed that circulates from an inlet port (opening 92), to the inside of the pipe 90, to an outlet port (aperture 63), to the outside of the pipe 90, and to an inlet port (opening 92).

On the other hand, the flow that moves beyond the projecting part 64 passes through the gap between the lower end face 72 of the rotor 70 and the upper face of each projecting part 64. Here, the interval CL1 between the lower end face 72 of the rotor 70 and the bottom 62 is an interval (about 50 µm) that does not allow aggregated cells pass therethrough. Accordingly, a shearing force is applied to aggregated cells included in the flow moving beyond the projecting part 64, between the rotating rotor 70 (the lower end face 72) and the fixedly-installed projecting part 64. Thus, the aggregated cells are dispersed into single cells. Then, single cells (and dispersed single cells) flow beyond the projecting part 64, in the flow moving beyond the projecting part 64 since the interval CL1 is large enough to allow single cells to pass therethrough. In this manner, more and more aggregated cells are dispersed, and aggregated cells in the biological specimen are dispersed into single cells, by circulating the circulating flow for a predetermined time period (about 60 seconds).

When the first dispersion process ends, in step S2, the preparation control unit 33 causes the sample pipetting unit 52 (see FIG. 3) to operate, and the sample pipetting unit 52 supplies the mixed solution containing the dispersed biological specimen, to the specimen loading part 31a of the supplementary detection unit 31. Accordingly, the mixed solution containing the dispersed biological specimen is sent to the flow cell 13 (see FIG. 5) of the supplementary detection unit 31. Then, in the supplementary detection unit 31, pre-measurement of the biological specimen (detection of the number of cells to be measured contained in the mixed solution) is performed through flow cytometry. As a result of the pre-measurement, concentration information reflecting the concentration of the cells to be measured (epithelial cells) contained in the mixed solution (biological specimen and preservative solution) is obtained, before main measurement for cancer determination is performed by the measuring apparatus 2.

After the pre-measurement has been performed, the preparation control unit 33 causes the mixed solution (biological specimen and preservative solution) to be discharged from the supplementary detection unit 31. Then, the concentration of the cells to be measured (epithelial cells) in the mixed solution (biological specimen and preservative solution) is calculated based on the obtained concentration information. Further, an aspiration amount of the mixed solution (biological specimen and preservative solution) for preparing a measurement specimen to be used in the main measurement is determined based on the calculated concentration. That is, based on the concentration (the number of cells to be measured per unit volume) of the cells to be measured in the biological specimen used in the pre-measurement and the significant number of cells necessary for detecting cancer cells in the main measurement, a collection amount (liquid amount) of the mixed solution (biological specimen and preservative solution) that is necessary for performing the main measurement and ensuring the significant number of cells is calculated.

Next, in step S3, a separation/substitution process is performed on the mixed solution (biological specimen and preservative solution) having the calculated collection amount (liquid amount). That is, as shown in FIG. 3, the preparation control unit 33 causes the sample pipetting unit 52 to operate, and the sample pipetting unit 52 aspirates the mixed solution (biological specimen and preservative solution) from the specimen holding chamber 51a1 of the first dispersion unit 51, by the calculated aspiration amount. When the aspirated mixed solution is supplied to the separation/substitution unit 53, the separation/substitution process is started.

In this separation/substitution process, the separation/substitution unit 53 substitutes, with a diluent, the preservative solution including alcohol as principal component, and separates the cells to be measured from the other cells and impurities. Further, during the separation, the liquid containing the cells to be measured is condensed, and the concentration of the cells to be measured is increased. As a result, a condensed solution is obtained in which the cells to be measured are concentrated so as to ensure the significant number of cells necessary for detecting cancer cells.

Next, in step S4, a dispersion process (second dispersion process) of aggregated cells in the condensed solution is performed by the second dispersion unit 55. Specifically, as shown in FIG. 3, the sample pipetting unit 52 aspirates the condensed solution in which the cells to be measured are concentrated, from the separation/substitution unit 53. In parallel with this, the container transfer unit 54 grips and takes out a measurement specimen container 7 set in a holder 57b of the reaction unit 57 to locate it at the specimen relaying part 52b. Then, the sample pipetting unit 52 moves above (above the specimen relaying part 52b) of the measurement specimen container 7 located at the specimen relaying part 52b, and supplies the condensed solution into the measurement specimen container 7. Then, the container transfer unit 54 transfers the measurement specimen container 7 containing the condensed solution to the second dispersion unit 55, and the second dispersion process is performed.

In the second dispersion process, as shown in FIG. 15, first, the container transfer unit 54 inserts a portion (lower part) of the measurement specimen container 7 into the liquid holding chamber 111 (the recess 114) of the second dispersion unit 55, and immerses it in the liquid 113 in the recess 114. Ultrasonic vibration is applied by the ultrasonic transducer 112 to the condensed solution in the measurement specimen container 7 being held and immersed in the liquid 113 in the recess 114 by the container transfer unit 54. The ultrasonic vibration is transmitted to the condensed solution through the liquid 113 and the measurement specimen container 7. This ultrasonic vibration causes cavitation (formation and then immediate implosion of fine bubbles) in the condensed solution, to disperse aggregated cells under the impact (pressure fluctuation) associated with the cavitation. Accordingly, aggregated cells (cells to be measured) remaining after the first dispersion process in the condensed solution in the measurement specimen container 7 are dispersed into single cells.

When the second dispersion process is completed, as shown in FIG. 3, the container transfer unit 54 sets a portion (lower part) of the measurement specimen container 7 into the setting port 56a of the liquid removing unit 56, while gripping the measurement specimen container 7. In the liquid removing unit 56, liquid drops attached to the external surface of the measurement specimen container 7 are removed, by supplying airflow to the external surface of the measurement specimen container 7. Then, the measurement specimen container 7 is set in a holder 57b of the reaction unit 57 (the rotatable table 57a) by the container transfer unit 54.

After the measurement specimen container 7 has been set in the reaction unit 57, in step S5, a process of removing RNA in the condensed solution is performed through addition of the reagent (RNAse) and heating. Specifically, the measurement specimen container 7 set on the rotatable table 57a is moved to the first reagent adding position P1, and a predetermined amount of the reagent (RNAse) is added to the condensed solution in the measurement specimen container 7 from the supply part 58c of the first reagent adding unit 58a. Then, the liquid in the measurement specimen container 7 is heated at a predetermined temperature (about 37° C.) for about 10 minutes in the reaction unit 57, whereby the RNA removal process is performed. It should be noted that during the about 10 minutes from addition of the reagent (RNAse) until completion of the reaction, the measurement specimen container 7 is moved to the second reagent adding position P2 by the rotatable table 57a.

After the RNA removal process, in step S6, a staining process of DNA in the cells to be measured in the measurement specimen container 7 is performed through addition of the reagent (stain solution) and heating. Upon completion of the RNA removal process, the measurement specimen container 7 is moved to the second reagent adding position P2 by the rotatable table 57a. In synchronization with this, a predetermined amount of the reagent (stain solution) is added into the measurement specimen container 7 from the supply part 58d of the second reagent adding unit 58b. Then, the liquid in the measurement specimen container 7 is heated at a predetermined temperature (about 37° C.) for about 1 minute by the reaction unit 57, whereby the DNA staining process is performed. It should be noted that during the about 1 minute from the addition of the stain solution until completion of the reaction (staining), the measurement specimen container 7 is moved to the aspiration position P3 of the specimen aspirating unit 59 by the rotatable table 57a.

Next, in step S7, the measurement specimen that has been subjected to the staining process is sent to the flow cell 13 of the primary detection unit 21, and the main measurement is performed on the cells in the measurement specimen. Upon completion of the staining process, the measurement specimen container 7 is moved to the aspiration position P3 for the specimen aspirating unit 59 by the rotatable table 57a. In synchronization with this, the pipette 59a of the specimen aspirating unit 59 is moved to the aspiration position P3. Accordingly, the measurement specimen is aspirated by the pipette 59a of the specimen aspirating unit 59 immediately after the completion of the staining process, without any other process interposed therebetween. Then, the aspirated measurement specimen is transferred from the specimen aspirating unit 59 to the flow cell 13 (see FIG. 5) of the primary detection unit 21, and the measurement control unit 23 (see FIG. 2) of the measuring apparatus 2 performs the main measurement on the cells in the measurement specimen. After the measurement specimen has been sent to the primary detection unit 21, the inside of the measurement specimen container 7 is cleaned by the container cleaning unit 66, and the cleaned measurement specimen container 7 will be used in a measurement process thereafter.

After the main measurement, in step S8, obtained measurement data is transmitted from the measurement control unit 23 of the measuring apparatus 2 to the data processing apparatus 4. The processing body 41 of the data processing apparatus 4 is constantly determining whether measurement data has been received from the measuring apparatus 2. Upon receiving measurement data from the measuring apparatus 2, in step S9, the processing body 41 of the data processing apparatus 4 performs a distinction process of particles in the measurement specimen based on the measurement data, and determines whether the cells to be measured (epithelial cells)

in the measurement specimen are abnormal, that is, whether they are cancerous cells (atypical cells). Then, the measurement process ends.

In the first embodiment, as described above, provided are the cell dispersion unit including the first dispersion unit 51 which performs the first dispersion process and the second dispersion unit 55 which performs the second dispersion process different from the first dispersion process; the primary detection unit 21 which detects characteristics information of predetermined cells contained in a biological specimen on which the first dispersion process and the second dispersion process have been performed; and the data processing apparatus 4 (the CPU 41a) which analyzes predetermined cells based on detection results. Accordingly, a plurality of dispersion processes of different types can be performed on the biological specimen. Therefore, even when cells in the biological specimen are aggregated at a high level, such cells can be effectively dispersed. Accordingly, even when cells are aggregated at a high level, the aggregated cells can be sufficiently dispersed into single cells, and thus, highly accurate cell detection can be performed. As a result, even when cells are aggregated at a high level, highly accurate cell analysis can be performed based on highly accurate detection results.

Further, as described above, the first embodiment is configured such that the amount of the biological specimen supplied by the sample pipetting unit 52 to the separation/substitution unit 53 is adjusted based on the detection result from the supplementary detection unit 31. In addition, the first dispersion process is performed before the detection by the supplementary detection unit 31. This configuration allows for preparation of a measurement specimen (concentrating the cells to be measured in the biological specimen) based on the detection results from the secondary detection unit 31 so that the measurement specimen contains the significant number of cells necessary for detecting atypical cells. This contributes to preparation of a measurement specimen suitable for detection in the primary detection unit 21. At this time, since the first dispersion process is performed before the detection by the supplementary detection unit 31, the detection by the supplementary detection unit 31 can be performed after aggregated cells are dispersed to some extent. As a result, accuracy of the detection by the supplementary detection unit 31 can be improved.

Further, as described above, the first embodiment is configured such that addition of the stain solution by the second reagent adding unit 58b is performed after the first dispersion process and the second dispersion process have been performed. According to this configuration, staining of cells can be performed after aggregated cells have sufficiently been dispersed into single cells through the first dispersion process and the second dispersion process. Thus, individually dispersed cells can be assuredly stained by the stain solution.

Further, as described above, the first embodiment is configured such that the biological specimen is processed by the first reagent adding unit 58a and the second reagent adding unit 58b after the first dispersion process and the second dispersion process; and detection by the primary detection unit 21 is performed after the processes by the first reagent adding unit 58a and the second reagent adding unit 58b, without any other process interposed therebetween. According to this configuration, the processes using the reagents including addition of the stain solution can be performed on single cells after aggregated cells have been dispersed through the first dispersion process and the second dispersion process. Since another process is not interposed between the processes using the reagents and the detection by the detection unit, cell detection can be performed immediately after processes using the reagents have been completed. As a result, cell detection can be quickly performed before cells to be detected are broken.

Further, in the first embodiment, as described above, the first dispersion process is a shearing force applying process of applying a shearing force to aggregated cells. This configuration actively causes aggregated cells to be dispersed through the shearing force, and thus, aggregated cells can be efficiently dispersed in the case of the biological specimen having a relatively large amount.

Further, in the first embodiment, as described above, the second dispersion process is an ultrasonic dispersion process of dispersing aggregated cells, by using ultrasonic waves. According to this configuration, ultrasonic waves can cause cavitation (formation and then immediate implosion of bubbles) in the biological specimen, to disperse aggregated cells. Since the bubbles generated by ultrasonic waves are fine, a uniform and scarcely-biased dispersion effect can be obtained, and damage to cells can also be suppressed during the dispersion processes.

Further, as described above, the first embodiment is configured such that the second dispersion process (ultrasonic dispersion process) is performed on the biological specimen having an amount smaller than that of the biological specimen on which the first dispersion process is performed. According to this configuration, the ultrasonic dispersion process can be performed on the biological specimen having a smaller amount, and thus, the second dispersion unit 55 can be downsized. The downsizing of the second dispersion unit 55 can reduce generation and the like of noises due to generation of ultrasonic waves. Further, by performing the ultrasonic dispersion process on the biological specimen having a smaller amount, ultrasonic vibration can be easily and uniformly applied to the entire biological specimen, and thus, a high dispersion effect can be easily obtained.

Further, as described above, the first embodiment is configured such that the first dispersion process is a shearing force applying process, the second dispersion process is an ultrasonic dispersion process, and the second dispersion process is performed after the first dispersion process has been performed. This configuration allows for efficiently established dispersion of cells, even when the cells are aggregated at a high level since it initially applies a shearing force to the cells to actively cause them to be dispersed. Furthermore, the ultrasonic dispersion process can be applied to the residual aggregates of cells, which individually have relatively small number of cells therein after the shearing force applying process, resulting in dispersion of the residual.

Further, in the first embodiment, as described above, the primary detection unit 21 includes: the flow cell 13 which allows the biological specimen to pass therethrough; the semiconductor laser 12 which emits light to the biological specimen passing through the flow cell 13; and the photodiode 15, the photomultipliers 18 and 19 which receive light generated by the semiconductor laser 12 emitting light to the biological specimen. According to this configuration, detection through flow cytometry can be performed on individual cells that have been effectively dispersed through the first dispersion process and the second dispersion process. Therefore, detection accuracy of the flow cytometry can be improved.

Further, as described above, the first embodiment is configured such that the primary detection unit 21 detects epithelial cells contained in the biological specimen, and the data processing apparatus 4 (the CPU 41a) analyzes whether the detected epithelial cells are cancer cells (atypical cells). According to this configuration, it is possible to obtain the cell analyzer 1 for detecting cancer cells (atypical epithelial cells) that can perform highly accurate cell detection irrespective of the aggregation level of the epithelial cells in the biological specimen, by performing a plurality of dispersion processes of different types on the biological specimen.

Further, in the first embodiment, as described above, the sample pipetting unit 52 is configured to dispense the biological specimen in the specimen holding chamber 51a on which the first dispersion process has been performed, to a measurement specimen container 7; and the container transfer unit 54 is configured to transfer the measurement specimen container 7 containing the biological specimen dispensed by the sample pipetting unit 52, to the second dispersion unit 55. According to this configuration, after the first dispersion process has been performed, the sample pipetting unit 52 can dispense, into the measurement specimen container 7, the biological specimen only by the amount necessary for detection by the primary detection unit 21, and the second dispersion process can be efficiently performed only on the biological specimen dispensed in the measurement specimen container 7.

Further, in the first embodiment, as described above, the container transfer unit 54 is configured to immerse the measurement specimen container 7 in the liquid 113 received in the liquid holding chamber 111, while gripping the measurement specimen container 7 containing the biological specimen dispensed by the sample pipetting unit 52. According to this configuration, the second dispersion process (ultrasonic dispersion process) can be performed, with the biological specimen contained in the measurement specimen container 7, without aspirating/discharging the biological specimen from/into the measurement specimen container 7. This eliminates the necessity of steps of aspirating and discharging the biological specimen, and thus the time necessary for the second dispersion process can be shortened. Therefore, it is possible to suppress increase of damage on the cells to be measured before they are subjected to the detection by the primary detection unit 21.

Second Embodiment

Next, with reference to FIGS. 2, 5 and 17, a second embodiment of the present invention will be described. In the second embodiment, a third dispersion unit 205 which performs a dispersion liquid adding process is added to the first embodiment which includes: the first dispersion unit 51 which performs the first dispersion process being the shearing force applying process; and the second dispersion unit 55 which performs the second dispersion process being the ultrasonic dispersion process. Since the other configurations than the third dispersion unit 205 are the same as those of the first embodiment, description thereof will be omitted.

Figure 17:
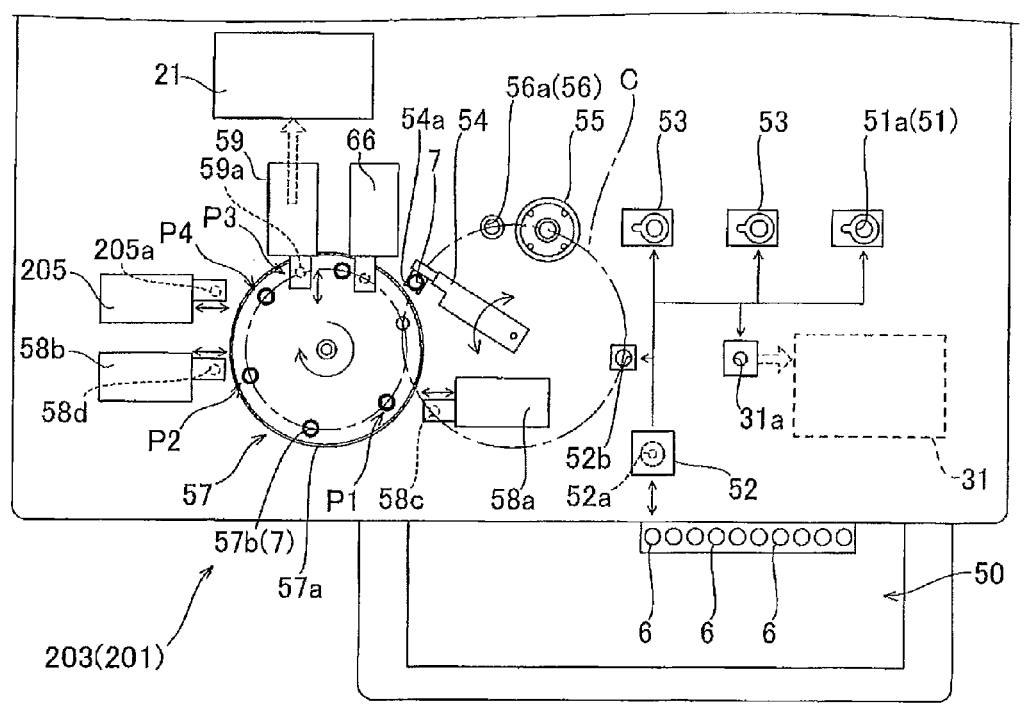
FIG. 17 is a schematic diagram showing an arrangement, seen in a plan view, of components of the measuring apparatus of the cell analyzer according to a second embodiment of the present invention.

As shown in FIG. 17, a measuring apparatus 203 of a cell analyzer 201 according to the second embodiment is provided with the third dispersion unit 205 which performs a third dispersion process, in addition to the first dispersion unit 51 and the second dispersion unit 55.

The third dispersion unit 205 has a function of performing the third dispersion process, which is different from the first dispersion process and the second dispersion process, on the biological specimen on which the first dispersion process by the first dispersion unit 51 and the second dispersion process by the second dispersion unit 55 have been performed. In the second embodiment, the third dispersion process is a dispersion liquid adding process of adding a dispersion liquid to the biological specimen to disperse aggregated cells. Specifically, the third dispersion unit 205 is configured to add the dispersion liquid in the measurement specimen container 7, after the second dispersion process by the second dispersion unit 55 has been performed, and then addition of the reagent (RNAse) by the first reagent adding unit 58a and addition of the reagent (stain solution) by the second reagent adding unit 58b have been performed, and immediately before the specimen is sent to the primary detection unit 21.

Specifically, in the second embodiment, the third dispersion unit 205 is installed at a position near the periphery of the rotatable table 57a of the reaction unit 57, and has a dispersion liquid supply part 205a which can move to a dispersion liquid adding position P4 above the measurement specimen container 7 set on the rotatable table 57a. Accordingly, when the measurement specimen container 7 has been transported to the dispersion liquid adding position P4 by the rotatable table 57a, a predetermined amount of the dispersion liquid can be added from the dispersion liquid supply part 205a into the measurement specimen container 7. In the second embodiment, the dispersion liquid is a surfactant. Through addition of the dispersion liquid, in addition to the first dispersion process and the second dispersion process, aggregated cells are chemically dispersed, and thus, the dispersion effect can be further improved.

After a measurement specimen container 7 is transported to the second reagent adding position P2 by the rotatable table 57a, a predetermined amount of the reagent (stain solution) is added from the supply part 58d into the measurement specimen container 7, and then the staining process is completed; the measurement specimen container 7 is transferred to the dispersion liquid adding position P4 by the rotatable table 57a. Then, immediately after the dispersion liquid adding process by the third dispersion unit 205, the measurement specimen container 7 is moved to the aspiration position P3, and the measurement specimen is aspirated by the pipette 59a of the specimen aspirating unit 59. Then, the aspirated measurement specimen is transferred from the specimen aspirating unit 59 to the flow cell 13 (see FIG. 5) of the primary detection unit 21 (see FIG. 2), and the main measurement on the cells in the measurement specimen is performed.

The other configurations of the second embodiment are the same as those of the first embodiment.

In the second embodiment, as described above, in addition to the first dispersion process and the second dispersion process, the dispersion liquid adding process is performed in which a surfactant as the dispersion liquid is added to the biological specimen to disperse aggregated cells. According to this configuration, aggregated cells can be chemically dispersed into single cells, through addition of the surfactant. Further, in the second embodiment, the measurement specimen is transferred to the primary detection unit 21 immediately after the surfactant has been added as the dispersion liquid. Thus, cell detection can be performed by the primary detection unit 21 before cells are broken by the surfactant.

Other effects of the second embodiment are the same as those of the first embodiment.

It should be noted that the embodiments disclosed herein are merely illustrative in all aspects and should not be considered as being restrictive. The scope of the present invention is defined not by the description of the above embodiments but by the claims, and includes meaning equivalent to the claims and all modifications within the scope.

For example, the first and the second embodiments have shown an example in which the present invention is applied to the cell analyzer 1 (201) which analyzes epithelial cells of the uterine cervix. However, the present invention is not limited thereto. The present invention may be applied to a cell analyzer that analyzes cells other than epithelial cells of the uterine cervix.

Further, the first embodiment has shown an example in which the first dispersion unit which performs the shearing force applying process and the second dispersion unit which performs the ultrasonic dispersion process are provided, and the second embodiment has shown an example in which the third dispersion unit which performs the dispersion liquid adding process is further provided. However, the present invention is not limited thereto. In the present invention, any two of the shearing force applying process, the ultrasonic dispersion process, and the dispersion liquid adding process may be performed. For example, the shearing force applying process and the dispersion liquid adding process may be performed. Further, a dispersion process that is different from the shearing force applying process, the ultrasonic dispersion process, and the dispersion liquid adding process may be performed. Further, four or more different dispersion processes may be performed.

Further, the first and the second embodiments have shown an example in which after the shearing force applying process by the first dispersion unit has been performed, the ultrasonic dispersion process by the second dispersion unit is performed. However, the present invention is not limited thereto. In the present invention, the shearing force applying process may be performed after the ultrasonic dispersion process has been performed. Alternatively, the first dispersion process (shearing force applying process) and the second dispersion process (ultrasonic dispersion process) may be simultaneously performed. As an exemplary configuration in which the shearing force applying process and the ultrasonic dispersion process are simultaneously performed, while the shearing force applying process is being performed on the biological specimen in the specimen holding chamber 51a of the first dispersion unit 51, ultrasonic vibration may be applied to the biological specimen in the specimen holding chamber 51a.

Further, in the first and the second embodiments, the first dispersion process (shearing force applying process), the second dispersion process (ultrasonic dispersion process), and the third dispersion process (dispersion liquid adding process) are performed on the biological specimen at different places. However, these processes may be performed on the biological specimen at the same place. For example, while the shearing force applying process is being performed on the biological specimen in the specimen holding chamber 51a of the first dispersion unit 51, the dispersion liquid may be supplied into the specimen holding chamber 51a; or while the ultrasonic dispersion process is being performed on the biological specimen in the measurement specimen container 7 in the second dispersion unit 55, the dispersion liquid may be supplied into the measurement specimen container 7. Further, while the shearing force applying process and the ultrasonic dispersion process are being performed on the biological specimen in the specimen holding chamber 51a of the first dispersion unit 51, the dispersion liquid may be supplied into the specimen holding chamber 51a. In such configurations, it is possible to simultaneously perform the shearing force applying process and the dispersion liquid adding process; the ultrasonic dispersion process and the dispersion liquid adding process; or the shearing force applying process, the ultrasonic dispersion process, and the dispersion liquid adding process.

Similarly, the second embodiment has shown an example in which the dispersion liquid adding process by the third dispersion unit is performed after the addition of the stain solution. However, the present invention is not limited thereto. In the present invention, the dispersion liquid adding process by the third dispersion unit may be performed immediately before the addition of the stain solution (staining process), or the dispersion liquid adding process may be performed simultaneously with the addition of the stain solution. Further, the dispersion liquid adding process may be performed before addition of the reagent (RNAse) is performed by the first reagent adding unit. Other than these, for example, the dispersion liquid adding process may be performed before the first dispersion process by the first dispersion unit; or before the separation/substitution process by the separation/substitution unit after the first dispersion process. In such a case, since the added dispersion liquid is substituted by the diluent by the separation/substitution unit, it is possible to reduce influence of the dispersion liquid on the ability, of the cells to be measured, to be stained by the stain solution.

It should be noted that in the first embodiment has shown an example in which the user performs preprocessing such as adding NAC as the dispersion liquid, before the analysis by the cell analyzer is started. However, in the present invention, the cell analyzer may be configured to perform this preprocessing as the dispersion liquid adding process.

Further, the second embodiment has shown an example in which the surfactant is added as the dispersion liquid. However, the present invention is not limited thereto. For example, an enzyme agent or a mucus remover may be used as the dispersion liquid.

Further, the first embodiment has shown an example in which the first dispersion process is performed before the separation/substitution process, and the second dispersion process is performed after the separation/substitution process. However, the present invention is not limited thereto. In the present invention, both of the first dispersion process and the second dispersion process may be performed before or after the separation/substitution process.

Further, the first embodiment has shown an example in which the second dispersion process (ultrasonic dispersion process) is performed on the biological specimen (biological specimen after being condensed by the separation/substitution unit) having an amount smaller than that of the biological specimen on which the first dispersion process (shearing force applying process) is performed. However, the present invention is not limited thereto. In the present invention, the second dispersion process may be performed on the biological specimen having the same amount as that is subjected to the first dispersion process.

Further, the first embodiment has shown an example in which the measurement specimen is aspirated by the specimen aspirating unit immediately after the staining process has been completed, without any other process interposed therebetween, and the measurement (main measurement) by the primary detection unit is performed. However, the present invention is not limited thereto. In the present invention, the measurement (main measurement) by the primary detection unit may be performed after the staining process has been completed and then another process is performed. However, in terms of improving the detection accuracy by the primary detection unit, it is preferable that the measurement (main measurement) by the primary detection unit is performed as soon as possible after the staining process has been completed.

Further, the first embodiment has shown an example in which the primary detection unit is provided which is composed of the flow cytometer including the flow cell, the semiconductor laser (light source part), and the photodiode and the photomultiplier (light receiver). However, the present invention is not limited thereto. In the present invention, a detection unit other than the flow cytometer may be provided.

It should be noted that various dimensions (the intervals CL1 and CL2, the thickness t1 of the bottom (projecting part), the depth t2 of the liquid retaining part, etc.) in the above embodiments are merely examples, and the present invention is not limited thereto. Dimensions of such parts may be changed in accordance with the amount of the biological specimen to be subjected to the dispersion process at one time, and the type of the cells to be subjected to the dispersion process.

Further, in the first embodiment, the shearing force applying process is performed as the first dispersion process and the ultrasonic dispersion process is performed as the second dispersion process. However, the dispersion liquid adding process may be performed instead of the shearing force applying process or the ultrasonic dispersion process.

What is claimed is:

1. A cell analyzer comprising:
    a first dispersion unit including a grooved rotor that disperses aggregated cells in a biological specimen through a shearing force applied by the grooved rotor to the aggregated cells,
    a first detection unit including a first flow cytometer that detects the cells in the biological specimen on which the shearing force is applied;
    a specimen preparation unit that separates a portion of the biological specimen based on a detection result from the first detection unit, and provides a measurement specimen;
    a second dispersion unit including an ultrasonic wave generator that disperses the aggregated cells in the measurement specimen by ultrasonic waves emitted from the ultrasonic wave generator;
    a second detection unit including a second flow cytometer that detects characteristics information reflecting properties of the cells in the measurement specimen on which the ultrasonic dispersion process has been performed; and
    an analysis unit which analyzes the cells in the measurement specimen, based on a detection result from the detection unit.

2. The cell analyzer according to claim 1 further comprising a stain solution supplying unit which supplies a stain solution for staining the cells, to the measurement specimen, wherein the stain solution supplying unit is configured to supply the stain solution to the measurement specimen after processing by the first and second dispersion units.

3. The cell analyzer according to claim 1, wherein the first dispersion unit further comprises:
    a specimen holding chamber that accommodates the biological specimen, and a pipe that accommodates the grooved rotor;
    an apertured member attached to an opening at an end of the pipe, the pipe including an opening in a side wall of the pipe; and
    wherein the first dispersion unit rotates the grooved rotor, with the grooved rotor and the pipe inserted into the specimen holding chamber, so as to cause the aggregated cells in the biological specimen to be transported by grooves in an outer surface the grooved rotor and dispersed while circulating the biological specimen in the specimen holding chamber between the apertured member and the opening in the side wall of the pipe.

4. The cell analyzer according to claim 1, wherein the specimen preparation unit reduces the amount of the biological specimen and the first dispersion unit is configured to perform the shearing force applying process on a first amount of the biological specimen, and the second dispersion unit is configured to perform the ultrasonic dispersion process on a second amount of the measurement specimen, the second amount being smaller than the first amount.

5. The cell analyzer according to claim 1 further comprising:
    a specimen dispensing unit which dispenses, into a specimen container, the biological specimen in the specimen holding chamber; and
    a container transfer unit which transfers, to the second dispersion unit, the specimen container containing the measurement specimen dispensed by the specimen dispensing unit.

6. The cell analyzer according to claim 5, wherein
    the second dispersion unit comprises a liquid holding chamber for accommodating a liquid to be subjected to ultrasonic waves, and
    the container transfer unit is configured to grip and transfer the specimen container, and is configured to immerse the specimen container in the liquid while gripping the specimen container.

7. The cell analyzer according to claim 1 further comprising a third dispersion unit that supplies a dispersion liquid to the measurement specimen to disperse the aggregated cells.

8. The cell analyzer according to claim 7, wherein the dispersion liquid comprises a surfactant.

9. The cell analyzer according to claim 1, wherein the first and second flow cytometers each comprise a flow cell that allows the biological or measurement specimen to pass therethrough, a light source that emits light to the biological or measurement specimen passing through the flow cell, and a light receiver that receives light generated when the light source emits light on the biological or measurement specimen.

10. The cell analyzer according to claim 1, wherein the aggregated cells comprise epithelial cells, and the analysis unit is configured to determine whether the epithelial cells are atypical.

* * * * *